(12) United States Patent
Robson et al.

(10) Patent No.: US 7,158,892 B2
(45) Date of Patent: Jan. 2, 2007

(54) GENOMIC MESSAGING SYSTEM

(75) Inventors: Barry Robson, Bronxville, NY (US); Richard Alan Mushlin, Ridgefield, CT (US)

(73) Assignee: International Business Machines Corporation, Armonk, NY (US)

( * ) Notice: Subject to any disclaimer, the term of this patent is extended or adjusted under 35 U.S.C. 154(b) by 932 days.

(21) Appl. No.: 10/185,657

(22) Filed: Jun. 28, 2002

(65) Prior Publication Data

US 2004/0006433 A1   Jan. 8, 2004

(51) Int. Cl.
*G06F 19/00* (2006.01)
*G05B 15/00* (2006.01)
*G11C 17/00* (2006.01)

(52) U.S. Cl. .............................. 702/20; 700/1; 365/94
(58) Field of Classification Search .................. 702/20; 700/1; 365/94
See application file for complete search history.

(56) References Cited

U.S. PATENT DOCUMENTS 5,963,646 A * 10/1999 Fielder et al. .............. 380/259

FOREIGN PATENT DOCUMENTS

WO   WO 9731327   *   8/1997

OTHER PUBLICATIONS

George J. Annas, "A National Bill of Patients' Rights," The New England Journal of Medicine, vol. 338, No. 10, Article 2, 157-165, (Mar. 5, 1998).
M. Morris Mano, "Computer System Architecture," Second Edition, 80-82 (1982).
Robson et al., "Natural Sequence Code Representations for Compression and Rapid Searching of Human-Genome Style Databases," Cabios, vol. 8, 283-289, (1992).

* cited by examiner

*Primary Examiner*—John S. Brusca
(74) *Attorney, Agent, or Firm*—Ryan, Mason & Lewis, LLP

(57) ABSTRACT

A computer-based method is provided for transferring data that includes a genomic sequence. The method includes identifying at least one genomic base in an input data stream comprising said genomic sequence; assigning a base-specific binary code to the at least one genomic base; grouping the base-specific binary code to form a genomic data stream representative of the genomic sequence; assigning a command binary code to at least one command for selectively processing said genomic data stream; and integrating said genomic data stream and said command binary code to form an output binary data stream.

41 Claims, 5 Drawing Sheets

GMS SEND-SIDE ARCHITECTURE

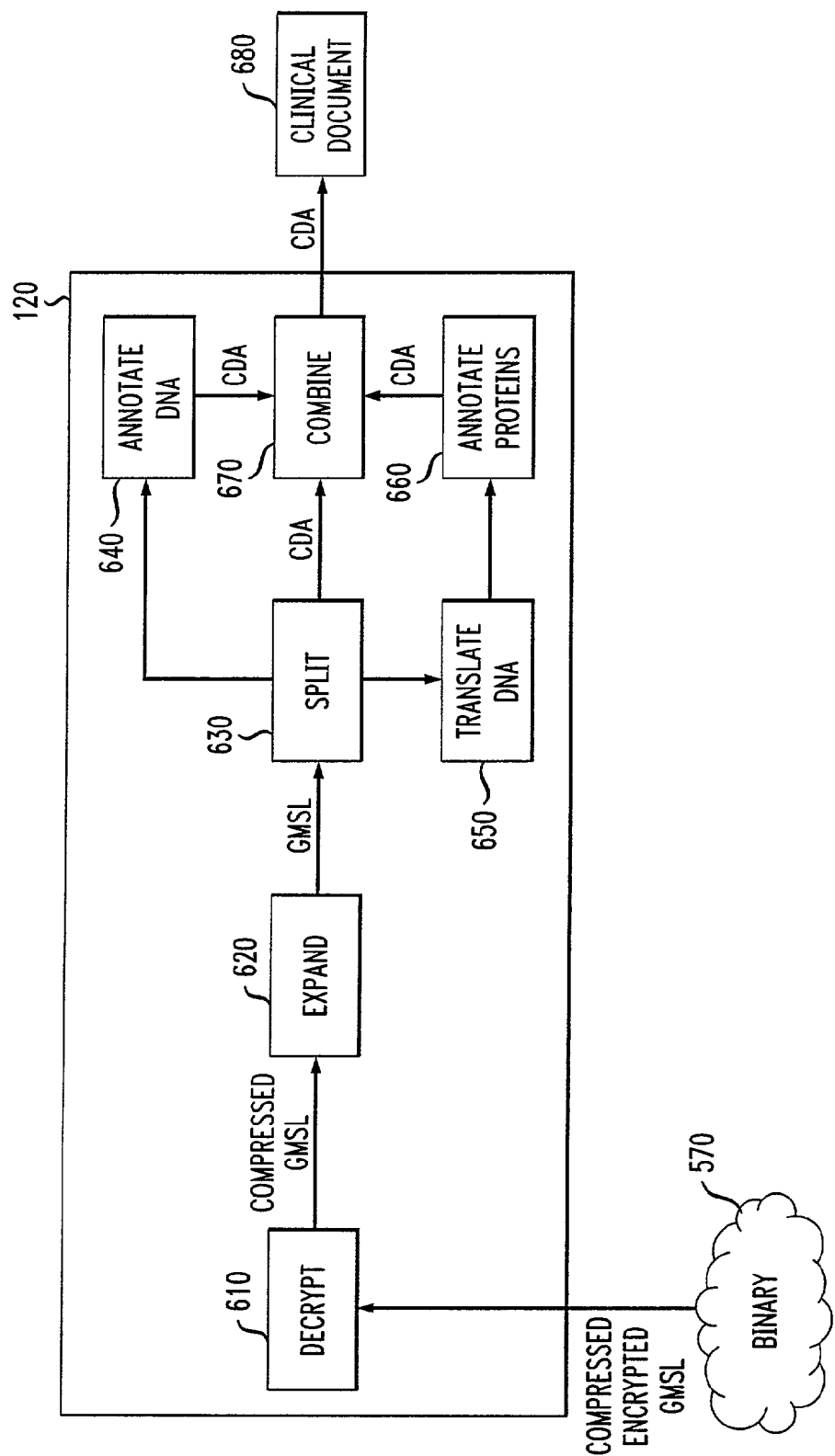

GENOMIC MESSAGING SYSTEM

FIELD OF THE INVENTION

The present invention relates to the electronic transmission of data and, more particularly, to a computer-based method for processing data that includes a genomic sequence.

BACKGROUND OF THE INVENTION

Sequencing the human genome and recent advances in the field of bioinformatics suggests that medicine of the future will take advantage of genomic data. For example, researchers and health care providers anticipate the ability to design drugs or at least screen a variety of drugs based upon the drug's ability to bind to a protein coded for by a patient's gene sequence. In order for this vision to become a reality, a tight linkage is necessary between a patient's personal genomic and expression data and a patient's medical records and the ability to access those records.

In addition, the Internet is already widely used to obtain medical information. Medical data are among the most retrieved information over the Internet, estimated at about 34–43%. With a projection of one billion individuals on the Internet by the year 2005, new challenges will be presented in efficiently transporting such volumes of medical and genomic data. Computers and the Internet are also being utilized more and more frequently for data mining of genomic sequences. This increased volume will demand more efficient way to forward genomic information and other information related thereto.

Conventional methods of electronically transmitting genomic data forward the data as unstructured text. For example, in order to transmit a DNA sequence electronically, the sequence first needs to be translated into a series of letters of the alphabet which represent the various DNA bases, i.e., A G T C. These letters of the alphabet must, in turn, be converted into a binary code in order to be transmitted and read electronically as ASCII text. Upon receipt, the code must be translated into the various letters of the alphabet which can represent the DNA sequence. This transmission of a DNA sequence as ASCII text can cause such transmissions to be unnecessarily slow and more prone to errors and unauthorized access. In addition, such conventional systems are unable to incorporate clinical information or annotation along with the genomic information.

Accordingly, a need exists for an improved method for transferring data that includes a genomic sequence in a data processing system and making the genomic data efficiently and safely miscible with other required information.

SUMMARY OF THE INVENTION

The present invention provides solutions to the needs outlined above, and others, by providing improved techniques for processing data that includes a genomic sequence, such as DNA or RNA, as will be described in greater detail below.

The method includes identifying one or more genomic bases in an input data stream that includes the genomic sequence. The input data can include clinical data, in addition to genomic data. This clinical data can, in turn, be encoded, along with the genomic data, and become part of the output binary stream. The method further includes assigning a base-specific binary code to the one or more bases, and grouping the binary code to form a genomic data stream representative of the genomic sequence. Preferably, the base-specific binary code is a 2-bit binary code that is grouped into 8-bit bytes, although other variations are possible. The method also includes assigning a command binary code to one or more commands for selectively processing the genomic data stream, and integrating the genomic data stream and the command binary code to form an output binary data stream. This integration provides a rich but self-consistent method for embedding signals in a DNA or RNA data stream, handling such aspects as compression, validation, encryption, selective security (i.e. making parts of the data available to people having certain passwords only from a set of passwords), annotation, addition of data such as image data, and transmission of embedded applets or other programming coded for more complex actions, such as displaying or upgrading recipient software.

In a preferred embodiment, the method further includes transmitting the output binary stream to a receiving data processing system. The receiving data processing system can then perform the steps of parsing the genomic data stream from the output binary code, unpacking the base-specific binary code within the genomic data stream; reassigning the genomic bases to the base-specific binary code; and arranging the genomic bases to form an output data sequence that includes the genomic sequence.

The bytes within which the binary code is grouped can include a genomic base portion and a command portion. For example, the genomic base portion may take up 6 bits and the command portion may be 2 bits of an 8-bit byte, and vice versa. The command portion may indicate a multiplicity of the bases. For example, 1, 2 or 3 bases may be represented by the 2-bit binary code grouped into an 8-bit byte, and the remaining bits of the 8-bit byte can signal the number of times those bases are repeated in the sequence. Alternatively, four bases represented by the 2-bit binary code can be grouped into the 8-bit byte and the multiplicity of the four bases may be specified elsewhere in the output binary data stream.

In a preferred embodiment, the method further includes encrypting the output binary stream. The output binary stream can then be decrypted, for example, after transmission.

As indicated above, the command binary code for selectively processing the genomic data stream can perform many different processing functions on the genomic data stream.

In a preferred embodiment, the command can include annotation text which annotates the one or more genomic bases. This annotation text can be embedded in the output binary data stream so as to preserve the relationship between the annotation text and the genomic bases. The command can include a text identifier. A corresponding text identifier can then be supplied to the user of the receiving data processing system.

The command can be operable to provide validation of integrity of the genomic data stream. The command can be operable to exclude identifying information pertaining to a person whose genomic sequence is contained in the genomic data stream from being revealed in the output binary data stream. The command can be operable to control the level of encryption of the output binary data stream. For example, the command can be recognized by a receiving data processing system to permit decryption of the output binary data stream. The command can be operable to seed an algorithm used for encryption, or to specify a block size of a shuffling algorithm used for encryption. The command can be operable to embed program code for selectively processing the genomic data stream. The command can also be operable to bracket at least one portion, or overlapping portions, of the genomic data stream for selecting such portion(s) for processing.

The techniques of the invention avoid many of the limitations of conventional techniques. First, the invention permits a genomic sequence to be transmitted more quickly, efficiently, and accurately. The present invention permits the practical transmission and storage of genomic bases of a genomic sequence when assigned a base-specific binary code, thereby avoiding the necessity of transmitting the sequence as text. In addition, unlike conventional systems, the invention permits the incorporation of clinical information or annotation within the output data stream containing the genomic information.

Clinical bioinformatics is distinct from conventional bioinformatics in that clinical bioinformatics concerns the genomics and clinical record of the individual patient, as well as of the collective patient population. Thus, there are not only medical research applications, but also healthcare IT applications, including potentially those in the category of e-health, which could benefit from the invention.

Though the present invention has value for genomics and bioinformatics in general, clinical application of genomics and bioinformatics requires special consideration for the privacy of the patient (see, e.g., Gerge J. Annas "A National Bill of Patients' Rights", in "The Nation's Health" 6th edition, eds. P. R. Lee & C. L. Estes, Jones and Bartlett Publishers, Inc. 2001), safety of the patient, and for informed decisions by the patient and physician. The recent federal Health Insurance Portability and Accountability Act (HIPPA) has been introduced to enforce the privacy of online medical data such that transmission, storage and manipulation of patient genomic and other data demands must now by some means recognize the importance of these concerns.

Since the system of the invention may be involved in a variety of medical care scenarios, including emergency medical care, it has been designed to be minimally dependent on other systems, when portability and performance are paramount. The messaging network can include direct communication between laptop computers or other portable devices, without a server, and even the exchange of floppy disk as the means of data transport. Basic tools for reading unadorned text representation of the transmission can be built in and used should all other interfaces fail.

Another advantage of the invention is that it can conform to clinical information technology standards recommended by the Health Level Seven organization (HL7). HL7 is a not-for-profit ANSI-Accredited Standards Developing Organization that provides standards for the exchange, management, and integration of data that supports clinical patient care and the management, delivery and evaluation of healthcare services. For example, HL7 has proposed a Clinical Document Architecture (CDA), which is a specific embodiment of XML for medical application. Although HL7 is the prominent standards body, aspects of these standards are in a state of flux. For example, there are few if any recommendations from HL7 in regard to genomic information. The invention provides the flexibility necessary to accommodate this uncertainty.

BRIEF DESCRIPTION OF THE DRAWINGS

FIG. 6 illustrates a receive-side architecture according to an embodiment of the invention.

DETAILED DESCRIPTION OF THE PREFERRED EMBODIMENTS

The present invention will be illustrated below in the context of an illustrative genomic messaging system (GMS). In the illustrative embodiment, the invention relates to the sending and receiving of DNA sequence data. However, it is to be understood that the present invention is not limited to such a particular application and can be applied to other data relating to a genome including, for example, RNA sequences.

The GMS relates to software in the emergent field of clinical bioinformatics, i.e., clinical genomics information technology concentrating on the specific genetic constitution of the patient, and its relationship to health and disease states. For example, when a message specifying a patient's DNA sequence is received by GMS, the system can add automatic annotation to the DNA, translate the DNA into protein sequences, and automatically annotate those, while preserving the content and location of any existing annotation sent with the original message.

Figure 1:
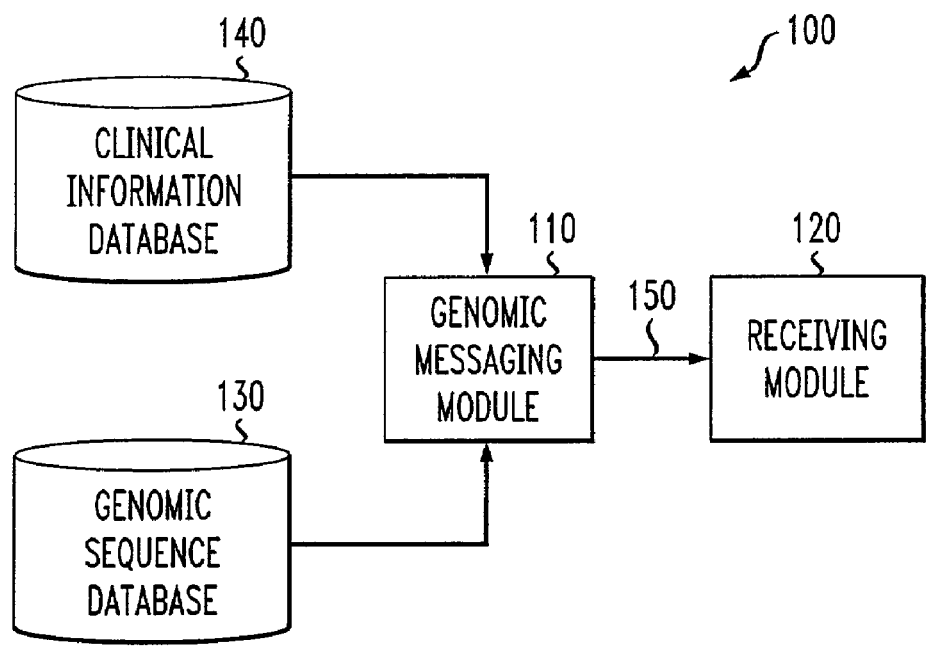
FIG. 1 illustrates a genomic messaging system (GMS) according to an embodiment of the present invention.

A block diagram of a GMS according to an embodiment of the present invention is shown in FIG. 1. The illustrative system 100 includes a genomic messaging module 110, a receiving module 120, a genomic sequence database 130 and, optionally, a clinical information database 140. As will be explained in detail below, the genomic messaging module 110 receives an input sequence from the genomic sequence database 130 and, optionally, clinical data from the clinical information database 140. The genomic messaging module packages the input data as further described below to form an output binary data stream 150 which is transmitted to a receiving module 120.

Figure 2:
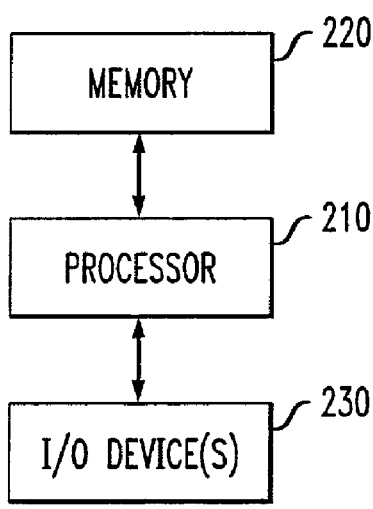
FIG. 2 is a block diagram of an exemplary hardware implementation of a GMS of the present invention.

FIG. 2 is a block diagram of an exemplary hardware implementation of the genomic messaging system 100. As shown, the system 100 may be implemented in accordance with a processor 210, a memory 220 and I/O devices 230. It is to be appreciated that the term "processor" as used herein is intended to include any processing device, such as, for example, one that includes a central processing unit (CPU). The term "memory" as used herein is intended to include memory associated with a processor or CPU, such as, for example, RAM, ROM, a fixed memory device (e.g., hard drive), a removable memory device (e.g., diskette), flash memory, etc. In addition, the term "input/output device" or "I/O device" as used herein is intended to include, for example, one or more input devices, e.g., keyboard, for inputting data to the processing unit, and/or one or more output devices, e.g., CRT display and/or printer, for presenting output data associated with the processing unit. It is also to be understood that the term "processor" may refer to more than one processing device and that various elements associated with a processing device may be shared by other processing devices. Accordingly, software components including instructions or code for performing the methodologies of the invention, as described herein, may be stored in one or more of the associated memory devices (e.g., ROM, fixed or removable memory) and, when ready to be utilized, loaded in part or in whole (e.g., into RAM) and executed by a CPU.

It is to be appreciated that, in an alternative embodiment, the invention may be implemented in a network-based implementation. For example, the user may submit source data sequences (in lieu of a separately stored genomic sequence database 130) at a remote client computer system, while the genomic messaging module 110 resides and is executed on a server computer system in communication with the client via a network, such as, for example, the Internet. The network could alternatively be a private network and/or a local network. Thus, a user operating remotely on his computer system, e.g., a personal computer, laptop and/or some other type of personal processing device, can enter genomic sequences through application software running on the computer system, e.g., web browsing software and/or graphical user interface associated with the system. The sequences can be passed over the network, in a conventional manner to the server. The server receives the sequences and executes the methodologies of the invention in order to package the data for transmitting to a receiving module. The output data can then be transmitted back to the client via the network or can be directly transmitted to a receiving module via the network. It is to be understood that the server may include more than one computer system. That is, one or more of the elements of FIG. 1 may reside on and be executed by their own computer system, e.g., with its own processor, memory and I/O devices. In an alternative configuration, the methodologies of the invention may be performed on a personal computer and transmit the output data directly to a receiving module, such as another personal computer, via a network without any server intervention. The output data can also be transferred without a network. For example, the output data can be transferred by simply downloading the data on, e.g., a floppy disk, and uploading the data on a receiving module. The general implementation preferably includes a web application platform, such as IBM WebSphere, a clinical document repository, such as the JIMR/XMLFS environment proposed by IBM Haifa, and public or private databases of genomic information, such as GenBank or First Genetic Trust.

Figure 3:
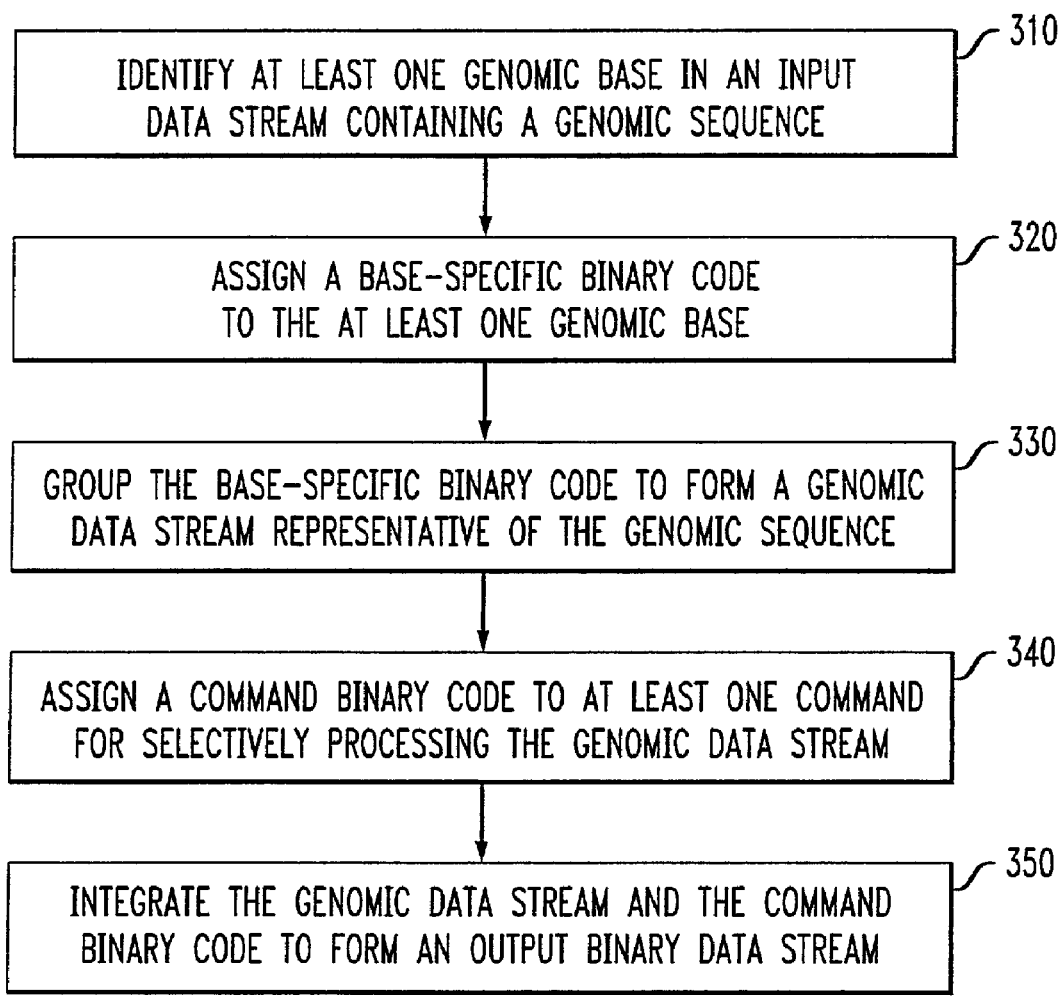
FIG. 3 is a flow diagram illustrating a GMS methodology according to an embodiment of the present invention.

FIG. 3 is a flow diagram illustrating the steps for processing data having a genomic sequence, in accordance with an illustrative embodiment of the invention. In step 310, one or more genomic bases are identified in an input data stream that includes a genomic sequence. A genomic sequence is defined herein to include one or a plurality of genomic bases. For example, if the genomic sequence is deoxyribonucleic acid (DNA), the bases can include purines—adenine and guanine, and pyrimidines—thymine and cytosine. If the genomic sequence is ribonucleic acid (RNA), the bases can include the purines—adenine and guanine, and the pyrimidines—uracil and cytosine. As indicated above, the genomic sequence can be obtained, for example, from public or private databases. The input data may also include clinical data.

Step 320 of FIG. 3 includes assigning a base-specific binary code to each of the one or more bases. A binary code is a group of n bits that assume up to $2^n$ distinct combinations of 1's and 0's with each combination representing one element that is being coded. Unlike the encoding of conventional ASCII (American National Standard Code for Information Interchange) text, the base-specific binary code specifically encodes genomic bases, e.g., A, T, G, C, or a group of genomic bases. ASCII, on the other hand, makes no distinction between genomic bases and the letters "A" "T" "G" "C" of the alphabet. This encoding step can include, for example, assigning a two-bit binary code to each of the four bases in a DNA or RNA sequence. For example, each of the four base types of a DNA sequence can be each represented by one of 00, 01, 10, 11. However, the base-specific binary code need not encode only one base at a time. The base-specific binary code can be representative of a plurality of genomic bases. For example, the base-specific binary code can represent groups of three genomic bases. Thus, a different base-specific binary code would represent each of the possibilities of grouping three genomic bases together. Such a binary code is referred to herein as a code group. One code group could represent AAA, while another represents AAG, etc. Using four possible genomic bases, e.g., A, T, G, C, there are 64 different possibilities for the groups of three bases. Therefore, using a binary code, 6 bits would be required to encode these 64 permutations. The same could be done for a set of base-specific binary codes that represents two genomic bases. By grouping two bases together in a code group, there are 16 different possibilities, requiring a minimum of 4 bits to represent these permutations in binary code.

In step 330 of FIG. 3, the binary code is then grouped, e.g., into bytes, preferably 8-bit bytes, to form a genomic data stream representative of the genomic sequence.

In step 340, a command binary code is assigned to one or more commands for selectively processing the genomic data stream. This command processing can include many functionalities, such as qualification, annotation, validation, encryption, selective levels of security to different persons, rendering anonymous patient identifiers, validation that correct data is being added for the page with an encrypted or unencrypted identifier, degrees of compression, automatic annotation, linkage to and invocation of other applications, and many other aspects. Indeed, the binary encoded approach can be extended to a full language-like capability for handling compression, validation, encryption, security, annotation, addition of data such as image data, and transmission of embedded applets or other programming coded for more complex actions, such as display or upgrading of recipient software.

In step 350, the genomic data stream and the command binary code is integrated to form an output binary data stream. The output binary data stream can then be efficiently and accurately transferred, for example, by downloading the data to a file or directly transmitting the data to a receiving processing system.

Figure 4:
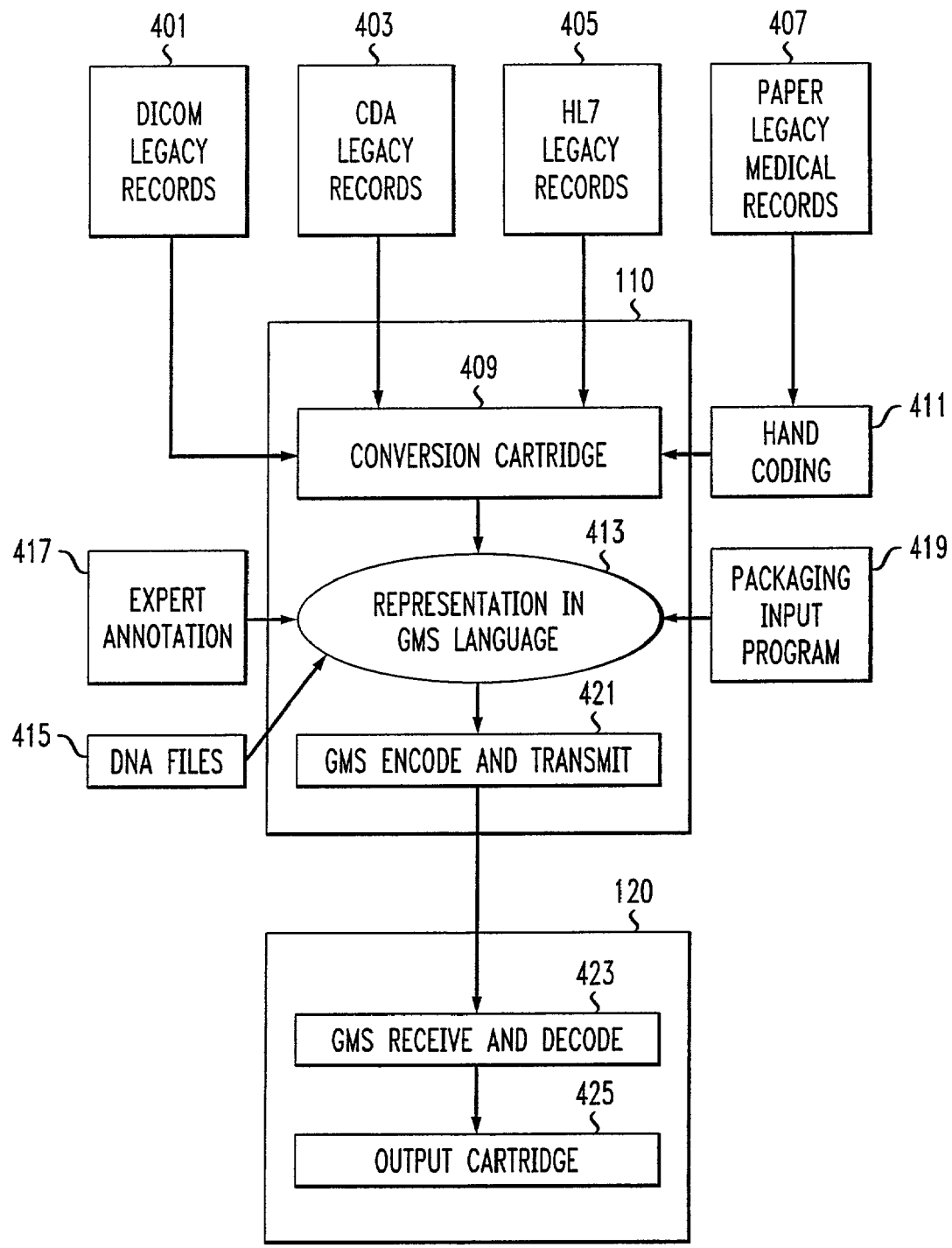
FIG. 4 is an illustration of how GMS may be coupled to various sources of clinical and genomic data.

FIG. 4 gives an overview example of how GMS can fit into the world of heterogeneous, autonomous, loosely coupled systems of clinical and genomic data. The boxes at the top of FIG. 4 show examples of clinical data repositories which conform to various degrees of standardization. These examples include, but are not limited to, Digital Imaging and Communications in Medicine (DICOM) legacy records 401, CDA legacy medical records 403, HL7 legacy records 405, and old paper legacy medical records 407.

These records can be converted by an automatic conversion cartridge(s) 409 into the GMS language 413. The conversion cartridge 409 can reside within the Genomic Messaging Module 110. In order to convert old paper legacy medical records into the GMS language, the records may first need to be hand coded 411. A separate GMS cartridge can be used for each type of clinical data repository and the cartridges can be automatic. These cartridges are adapters used by GMS to perform various input/output conversion tasks. For example, a conversion cartridge can be written in Perl and activated by the main GMS Perl Program, or GMS may support other cartridge implementations such as XSLT.

Data from genomic databases can be brought into the GMS via DNA files 415 which contain the raw DNA sequences and optionally, but importantly, allow annotation by an expert 417. The expert can annotate the DNA files directly with, for example, a text editor or other tool, and the modified DNA files can then be automatically converted into GMS language. The syntax of the DNA files prior to conversion is quite flexible and supports XML tags for annotation plus special GMS commands for process control.

In addition, a packaging input program 419 can be provided for packaging an application with the input data. On receipt of the GMS input data, the packaging input program 419, for example, a Perl program for displaying the data, is optionally extracted and run.

Once all the inputs are represented in GMS language, the step of encoding and transmission 421 begins. The GMS encoding process is a stream-oriented algorithm which results in a compact binary representation of the combined input data. The compact binary stream is optimized for compression of DNA sequences. Unlike the "natural" languages used for clinical data and program source code, DNA contains seemingly random distributions of characters, and so, being "information rich" by virtue of its distribution of characters, it does not compress well with standard techniques. GMS uses as few as 2 bits per base, the theoretical limit for the 4-characters representing the genomic bases (e.g., A G T C).

The encoding process includes the option of encrypting the binary stream using a scrambling algorithm. A key may be required at the receiving end to unscramble the stream. Different parts of the GMS encoded data can be encrypted using different keys.

The system can be configured such that the receiver must satisfy fairly stringent requirements when options for maximum security are set. For example, in the most demanding scenario, the receiver must know the number representing the level of encryption chosen, two tumbler key values associated with that encryption, a patient identifier in explicit or encrypted form, the nature of the terminator signal used to terminate partitions of the data, and, in some modes of use, whether text compression was applied to either upper or lower case, and every password and file-lock specifically coded in the system. Further, the receiver may be obliged to have at hand a "template" or "filler" file or files which complete the patient's DNA data. Whereas some of these latter defenses could be "hacked" by irregular access to the incoming data file if decrypted, some of them such as text compression and separate identifier encryption render more difficult the illicit decryption of the encrypted file. In addition, state-of-the-art industry standard encryption can be used to encode and decode the data stream between the encoding and decoding steps performed by the GMS system.

The encoded, compressed, encrypted binary stream can be output into a file on the transmitting system. In this state the stream can be transmitted by any means to the Receiving Module 120, where the decoding process takes place.

Once the encoding and transmission is complete, the data is then received and decoded 423 by the Receiving Module 120. The decoding process 423 decrypts and uncompresses the stream into the GMS internal representation. The decoding process 423 can also activate an output cartridge(s) 425 containing code to produce data in a form compatible with various applications. The output cartridge code can be executed the moment it is encountered and completed in the stream, or can optionally cause later execution. As well as modifying the output modes and displays, or allowing upgrades or repair patches to the receiver's GMS program, these embedded program codes can be used to alter many of the embodiments of the invention. The output cartridge can be written in any appropriate programming language, such as Perl or Java. The system readily allows extension to new program language types such that several different programming languages might be embedded in different parts of the genomic sequence.

One example of an output cartridge is a cartridge for translation of a DNA sequence or portions of the DNA sequence into an amino acid sequence, followed by the automatic annotation of the resulting proteins. Other examples of such output cartridges include, but are not limited to, a research database cartridge and a physician cartridge. In addition, the GMS representation of the data stream from an output cartridge can be converted, for example, into an XML file for use by other applications. It is preferred that such an XML output be as CDA compliant as possible.

It is useful to group the components of GMS into two categories: "core" components and "cartridge" components. The core performs the encode-, compress-, encrypt-, decrypt-, uncompress-, decode-cycle which begins and ends with all the data in the GMS language. The core components can be implemented, for example, as a single Perl executable program, with the choice between send and receive function determined by a runtime parameter. Once that choice is made, additional parameters can control input selection and encryption for the send function, and decryption and output selection for the receive function. The send function can be used, for example, by the "owner" of the data to be sent, as well as trusted parties such as the clinical bioinformaticist or referring physician. The receive function might be used, for example, by a consulting physician or researcher.

The cartridge components operate on the data either before or after processing by the core components. It is preferred that operation of the cartridges require little or no user interaction. Examples of cartridges for converting input and output have been mentioned above. Cartridges can be implemented, for example, as Perl scripts containing rules expressed using regular expressions. These scripts can be executed at runtime under the control of the core program but packaged as separate files. Some of these cartridges, such as the protein annotation example, might be considered mini-expert systems. In addition to the example cartridges referred to above, it is envisioned that other cartridges can be developed to become considerably more "expert," and proliferate to accommodate a wider variety of inputs and outputs as GMS development and deployment proceeds.

Figure 5:
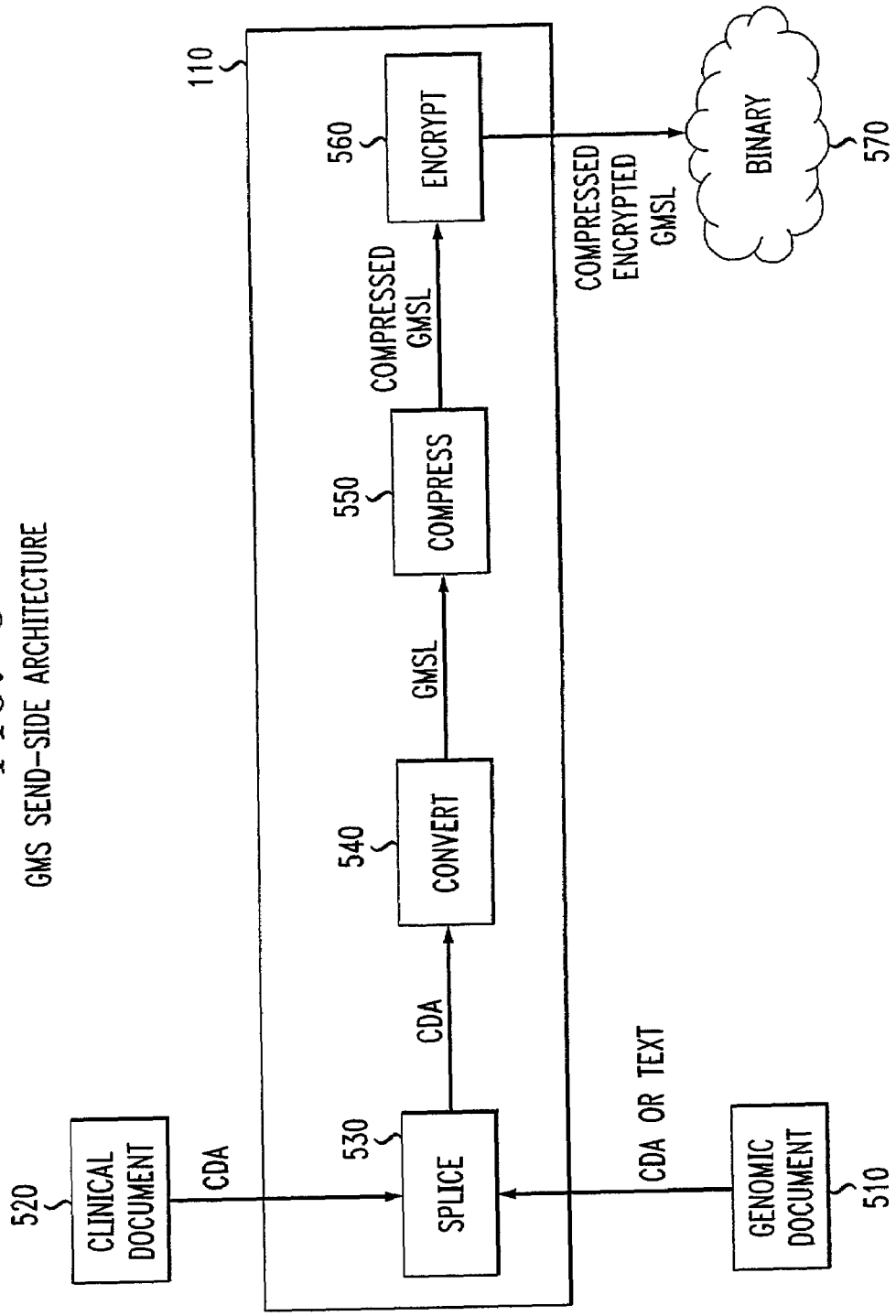
FIG. 5 illustrates a send-side architecture according to an embodiment of the invention.

The architecture of the GMS system can be divided into a send-side architecture and a receive-side architecture. FIG. 5 shows a send-side architecture in accordance with an illustrative embodiment of the invention. FIG. 6 shows a receive-side architecture in accordance with an illustrative embodiment of the invention.

In FIG. 5, genomic document(s) 510 and, optionally, clinical document(s) 520 are spliced 530 by the genomic messaging module. As discussed above, the clinical document(s) can be CDA compliant and the genomic document(s) can be CDA compliant or text. The spliced information also can remain CDA compliant. During step 540, the spliced data is converted into a genomic messaging system language (GMSL), which is discussed further below. In step 550, the genomic data in the data stream is compressed. This step is performed by assigning a binary code to each of the DNA bases such that each base has a unique binary code. The binary code is an n-bit binary code, where preferably 2≦n≦6. In a preferred embodiment, the binary code is a two-bit binary code. The binary stream is then packed into a stream of bytes, preferably 8-bit bytes. The compressed GMSL can then optionally be encrypted 560, such that the data is transmitted as a compressed, encrypted GMSL 570.

In FIG. 6, the compressed encrypted GMSL 570 is first decrypted. The compressed GMSL is then expanded (de-compressed) 620. This expansion step includes unpacking the bytes (preferably 8-bit bytes) back into the n-bit binary code (preferably 2-bit binary code). DNA bases are then reassigned to the binary code and the DNA bases are arranged in their original sequence. The data stream can then be split 630, for example, to annotate the DNA sequence 640 or to first translate the DNA sequence into a protein sequence 650 and annotate the protein 660. The annotated DNA and/or annotated protein sequence 660 can then be combined 670 to form, for example, a CDA compliant clinical document 680 that can be written to a data file.

Given a general description of the elements of the genomic messaging system of the invention and various exemplary implementations, various inventive methodologies will now be explained in detail. Although the functionalities of the GMS are described in the context of a genomic messaging system language, it is to be appreciated that one skilled in the art could utilize alternative computer language and commands to achieve the functionality of the invention.

For ease of reference, the remainder of detailed description will be divided into sections as follows: (I) Genomic Messaging System Language (GMSL); (II) GMS Command Usage; (III) Options with the GMS Messaging/Receiving Modules; (IV) Input; (V) Output; and (VI) GMS Language Commands.

I. Genomic Messaging System Language (GMSL)

GMSL is a novel "lingua franca" for representing a potentially broad assortment of clinical and genomic data for secure and compact transmission using the GMS. The data may come from a variety of sources, in different formats, and be destined for use in a wide range of downstream applications. However, GMSL is optimized for annotation of genomic data. This section explains the basic features of GMSL.

The primary functions of GMSL include:
Retaining such content of the source clinical documents as are required, and to combine patient DNA sequences or fragments.
Allowing the expert to add annotation to the DNA and clinical data prior to its storage or transmission.
Enabling addition of passwords and file protections.
Providing tools for levels of reversible and irreversible "scrubbing" (anonymization) of the patient ID etc.
Preventing addition of erroneous DNA and other lab data to wrong patient record.
Enabling various forms compression and encryption at various levels, which can be supplemented by standard methods applied to the final file(s).
Selecting methods of portrayal of the final information by the receiver, including choice of what can be seen.
Allowing a special form of XML-compliant "staggered" bracketing to encode DNA and protein features which, unlike valid XML tags, can overlap.

GMSL, like many computer languages, recognizes two basic kinds of elements: instructions (commands) and data. Since GMS is optimized for handling potentially very large DNA or RNA sequences, the structure of these elements is designed to be compact. The unit of processing as shown herein is an 8-bit byte, but this unit of processing can vary.

The individual bits can have significance as commands or data. This approach allows some bytes to be pure commands, some to be pure data, and some to be part command and part data. Such so-called "mixed commands" are actually commands which implicitly "represent" or invoke data.

The mixed type command is motivated by the fact that any of the four DNA bases can be represented using only 2 bits. Therefore, sequences of 1 (singlet or SNP), 2 (doublet), or 3 (triplet) bases can fit in a single byte, with 2 or more bits left to distinguish between the possible arrangements. Shown below are examples of four mixed commands for representing these cases.

| Case | Bits |
| --- | --- |
| Singlet (A, C, G, or T) | XX000100 |
| SNP (any 1 base) | XX100100 |
| Doublet (any 2 bases) | XXYY1100 |
| Triplet (any 3 bases) | XXYYZZ11 |

In this table, the 0's and 1's represent the commands, and the X's, Y's and Z's represent the 1, 2, or 3 bases expressed as 2 bits each, as follows:

A=00 G=01 C=10 T=11

It is convenient that this scheme allows a codon for an amino acid to be represented by the triplet case. It may also be useful, in terms of the performance of downstream applications, that the complementary bases can be the binary negations of each other, that the left bit distinguishes purine (0) from pyrimidine (1), and that bases with both bits identical (00, 11) have the stronger, triple hydrogen bonds, while those with different bits (01, 10) have weaker double hydrogen bonds.

Another class of command that relates to the byte mapping principle allows 4 bases to be packed into a single byte to give the most compressed stream. This feature is useful for handling long DNA sequences uninterrupted by annotation. The tight packing continues until a special termination sequence of non-DNA characters is encountered. This compressed data can either be transmitted in the main stream, or read from separate files during the decode process. These genomic "background" files are a key ingredient in the GMS security scheme. By transmitting the genetic "base" and "variations" separately, the individual's specific DNA sequence can be obscured from all except those having access to both parts.

Another type of mixed command can be used to open or close a "bracket," like parentheses, for grouping data together. These bracket commands can be used to delineate a particular stretch of a genomic sequence for processing. Unlike parentheses, or markup tags, which can only be "nested," e.g., {a[b(c)d]e}, GMS brackets can be crossed, e.g., {a[b(c}d)e]. This feature is important for genomic annotation because regions of interest often overlap. This feature also allows the same part of a sequence or overlapping parts of sequences to be processed, e.g., annotated or qualified, in a plurality of ways at the same time.

For example, a data statement as described below might immediately precede the open bracket to indicate that the sequence enclosed by the brackets should be read as RNA (e.g., that T is to be replaced by U, that the bases enclosed care experimentally uncertain, or that the G explicitly encoded might in fact be an A). Though these brackets map to self-standing XML tags, XML may not be the required output. When XML is not the required output, the XML file is simply ignored and attention paid directly to the stream transmitted or to a file reports.dat. This file describes the stream transmitted with automatically added comment to interpret the stream. Further, the action of an embedded applet or other programming code as described above can be used to assign specific meaning or special action to the brackets.

The mixed commands for brackets can be, for example:

| Open bracket  | xxxxxx01 |
| Close bracket | xxxxxx10 | where the 6-bit quantity "xxxxxx" is one of 64 possible bracket types, analogous to the characters '(' and ')', '[' and ']', '{' and '}', and '<' and '>', etc. As stated above, these concise binary codes can represent mutually overlapping or "staggered" brackets, e.g., as in sequence ([)], as well as mutually embedded brackets ([ ]), so as to qualify parts of the sequence by association with one or more further binary codes. Therefore, these brackets can be used to qualify sequence data, for example, to denote as being experimentally uncertain, annotate the sequence, or exert a special action on parts of the sequence. Such special action can be implemented by receiving the sequence data on file, e.g., stream.gmb or the encrypted form stream.gme, using an alternative application, by accessing the reports.dat file with the customary application, or by embedding one or more applets or other program code within the genomic data stream and using the current GMS implementation which automatically incorporates and executes such embedded code.

In addition to these "mixed" commands, there are commands which are not associated with any particular portion of the genomic sequence, as well as commands which are associated with a number of bytes of genomic data. Other than having the form XXXXX000, these commands have relatively arbitrary bit patterns. The use of these commands will be described in detail in the sections that follow. Using an 8-bit byte, there are 256 possible command bytes. One command can be reserved for switching to a 2-byte command set for future expansion. A special meaning can be assigned to the "null byte" 00000000, corresponding to the command "warning." Because of the way the command bit patterns have been assigned in the encode process, this particular bit pattern should not be encountered in uncompressed data outside of a data statement, and if it is, GMS will terminate with warnings.

Command codes can be primarily informational and more in the character of concise ways of standing for commonly occurring types of comment. For example, a special command can indicate that a deletion or insertion of a genomic base or a run of such base pairs occurs at that point, or that the symbol represents a polymorphism. The insertion or deletion command can have two components, analogous to a pair of brackets, such that the enclosed base pair symbols are indicated as the sequence of interest.

When sequences are experimentally unreliable at some location in the genomic sequence or it is experimentally unclear whether a particular base is, for example, A or G, the sequence can be interrupted by commands indicating that one reliable fragment is ended and that the subsequent fragment has a level of uncertainty. For that and other purposes, the ability for keeping track of multiple fragments is included within the invention, including the ability to introduce comment. GMS has the ability to keep count of the segments and, optionally, separate and annotate them in, for example, the XML output.

II. GMS Command Usage

The primary data is seen as DNA base sequences to be compressed, preferably three-to-a-byte. This triplet encoding conveniently maps directly to the amino acids of protein sequences. Specific encoding into one two symbols per byte can specifically be done by separating the symbols by semicolons or new lines. In the example

AGGC;TT;AGCCT the TT can be stored as a doublet in one byte, the rest as triplets as much as possible. With this field of DNA data, commands and generic DATA statements can appear separated by semicolons or new lines, and commands of multiple words are tolerant to placement and white space.

A command set for the GMSL is set forth in Section VI. Some exemplary commands for the GMSL include:

read in dna;

which reads in DNA from the specified file and compresses it 2 bits per base character, validate;

which may appear to represent and count validation points to ensure that they have been seen exactly N times, or danger;

which is normally wrapped in another environment and should not be seen deliberately. Two danger commands in succession will guarantee detecting a phase shift of incoming data by 1–7 bits. (The "danger" command can be encoded by 00000000 which is also the danger signal, and this string of bits will always be encountered by a phase shifted read encountering 0000000000000000).

A sample command phrase or group made up of several commands can be as follows:

password; [&7aDfx/b{by shaman protect data];
xml; [<gms: {patient}_dna>\];index;and protein;
filename[template.gms{by shaman unlock data}];read in dna
xml;[</gms: {patient}_dna>\];index;and protein;

Here the command password in the command phrase password; [&7aDfx/b{by shaman protect data], allows the incoming stream to be read and active from that point only if (a) the receiver has already entered a patient ID which encrypts to &7aDfx/b, and (b) if at that point the receiver enters another password, here shaman. Data item filename; [template.gms{by shaman unlock data}] allows the data of the file specified to be incorporated into the stream only if that password, here shaman, was the last entered, helping ensure that the correct file is loaded and ensuring that the field has not been intercepted and falsely continued by a hostile agent. Another password command, with a different password requested, could follow the first password request. The DNA on file in any event is effectively a filler template between the polymorphisms, and might be transmitted only once to the physician, so serving as a further kind of encryption key in the general sense. The xml command requests annotation in XML format: the tag names are calculated in part on receipt of the stream from the variable {patient}, specified elsewhere and here carrying the patient's name. This can be "scrubbed" into an encrypted form if an earlier specification was set. The XML tags are shipped with the stream. The command index includes them as tags in the output CDA XML file. The command and protein requests that this annotation be interlaced with the automated annotation of the DNA and of the resulting protein sequences explored in all six reading frames.

A valuable DNA/protein annotation command is of the example form (43 which forces onto the final XML output file the tag e.g. <open feature="whatever" type="43" level=8/>depending on the bracket level. The command is used to annotate overlapping features, for example, DNA and protein features, which are impermissible to XML (in the sense that to XML <A> <B> </B> </A> is XML -permissible, <A> <B> </A> </B> is not).

Generic DATA statements encode specific or general classes of data which include, for example:

```
data ;[ . . . /];
password ;[ . . . /];
filename;[ . . . /];
number ;[ . . . /];
xml;[ . . . /];                    (XML)
perl;[ . . . {end of data}]        (Perl applet executed on receipt)
hl7;[ . . . {end of data}]         (HL7 messages)
dicom;[ . . . {end of data}]       (images)
protein ;[ . . . /];
squeeze dna;* . . . /]             (compress DNA to 4 characters per
                                    byte.)
```

Alternative forms like data; /............/ are possible. The terminating bracket "]" is optional and is actually a command to parity check the contents of the data statement on receipt. Within the fields [.............................. can be inserted text permitted by "type." Type restriction is currently weak, but backslash would be prohibited in certain types of data to avoid the fact that it is a permissible symbol in content.

A wide variety of commands in curly brackets (French braces) can appear in these DATA fields, such as {xml symbols}, {define data}, {recall data}, {on password unlock data}, or carry variable names such as {locus} which are evaluated and macro-substituted into the data only on receipt.

The basic language can be used to make countless phrases out of their combinations, but there are relatively few complex commands formed. For example, the commands filedata; [{by shaman unlock data}]

number;[15 base pairs\]

squeeze dna

*

AGCTTCAGAGCTGCT\ place a protective lock on the following data, requiring a password (in this example "shaman") for access. The commands also compress 15 base pairs of DNA into four base pairs per byte as much as possible. Another example is:

name;[mary\];xml;[elizabeth {define data}]

xml; [<test>patient {identifier} has informal code name {mary}</test>\];index which illustrates both use of the use-defined variable "mary" and the system variable "identifier" (the current patient identifier) in writing specifically stated XML (the <test> tags and their content).

III. Options with the GMS Messaging/Receiving Modules

The sending (or encoding) and receiving (or decoding) components can be represented in the same program. The choice of decoding means that the user can see only the stream of bytes which has been received on a "gms stream" file. Encoding will invoke both encoding and a test decoding under full receiving conditions, guaranteeing that, if the receiver has the same software and file, and choice of passwords etc., that person will be able to interpret the file correctly and will see the effects at the screen intended by the encoder. Since the information stream sent can include Perl code and Perl applets, the identical code version can be sent. At decode time, not only routine (e.g. parity) checks can be performed, but all data in memory and in files created by the encoding and decoding steps can be compared byte for byte.

The GMS language file containing commands and data as described previously is compressed into a messaging stream which may be optionally further compressed and encrypted. Various options are available when starting the program.

These options include various mode and filename options. For example, mode options include a choice of encode (e) or decode (d) mode, plus choice of "root" name for the files used if the default name 'stream' is not satisfactory. There is also an optional template (t) mode. In this mode the system immediately walks the user through a master template example file asking the user to enter replacement data for the character string ???? whenever encountered.

The GMS provides a privacy option. For example, the user can determine whether the received document will contain the actual patient identification, or be "scrubbed" by replacing it with an encrypted identifier. A choice also exists between compression of either upper or lower case text into two characters per byte. Although this can save memory for extensive text, its primary function is to render unauthorized decryption more difficult.

The GMS also provides a terminator selection option. This is an option to replace part of the sequence of characters which represent a 'terminator', i.e. signifies the end of transmission of particular data field within the transmitted stream. The default is a limited number of terminators, some with command-like functions, of which {end of data} is the most basic, and all of which end in . . . data}. This option allows the word "data" to be replaced with a string of any length to ensure a terminator which is unlikely to be encountered by chance even in very large amounts of data, e.g., transforming the terminator {end of data} to {end of a very large amount of stuff}. A prior probability of this chance happening is reported when this option is used. No input files are permanently changed by this choice, but the receiver must know the choice.

The GMS also provides a choice of level of encryption, if any. The byte stream can be shuffled the specified number of times following a machine-independent "random number" generator linked to an iteration count of the generation to avoid recycling. The random number must be known to decode.

The GMS provides what are defined herein as "Tumbler Options." For example, "Tumbler One" is a choice of number seed which may be, for example, the Social Security Number of a patient. This number seed must be known to decode. "Tumbler Two" is a choice of size of blocks of bytes which may be shuffled (larger sizes speed encryption process). Decoding is performed using the same size blocks of bytes.

The GMS also provides an identifier option. The text input in the identifier not only affects the encryption, but on receipt can be compared with an encrypted string in the byte stream being decoded.

IV. Input

As described above, GMS can incorporate data from at least three different inputs before processing the data into a binary stream. The first input is the "clinical" data, which can come from a variety of sources, but is expected to be CDA compliant in the preferred implementation. The second input is "genomic" data, also from any source, in the form of DNA bases, optionally with annotation. This input is processed by inserting GMS commands. The third, and optional, input is a program, such a Perl program, to be transmitted with the data and run on receipt. Interfacing GMS to clinical and genomic data management systems involves adapting existing data sources to the input requirements of GMS.

These input routes can be bypassed by directly entering data into the primary GMS input file using GMSL syntax. This "free-form" approach involves the annotation of a DNA sequence or other clinical data, and instructions on how it is to be transmitted and seen by the receiver.

As mentioned above in Section III, the user can select a root filename (no extension) to be used for a complete GMS run. The extensions, or suffixes, for the various files are set by GMS convention. The primary input file is a .gmi (genomic messaging input) file, from which GMS automatically generates a .gms (genomic messaging system) file containing GMS commands and data expressed in the canonical GMSL representation. It is useful to think of the GMSL canonical representation (the .gms file) as (a) the final form which GMS uses to generate the encoded byte stream as a .gmb (genomic messaging binary) file, and (b) as the "lingua franca" and "Grand Central Station" for bringing together incoming data, from the primary input file (the .gmi file) and any secondary input files, which are described further below.

In cases of direct input, the user manually creates the content of the .gmi file. The appearance of this file will be very similar to the .gms file which is generated from it and which is converted to the stream of transmitted bytes. There are exceptions, such as when the files are affected by options requested on startup of the GMS system when the prepared .gmi file is first processed. Examples of this scenario include:

i. Text compression of upper or lower case text takes place in the generation of the .gms from the .gmi file.
  ii. The string {identifier} on the .gmi file can be used to stand for the identifier of a specific or generic patient which, optionally, is only made explicit when the .gms file is constructed or (when the "scrub" option is chosen) on receipt of the GMS message.
  iii. The occurrences of the terminator word data in the terminator signals {. . . data} can be altered in generating the .gms file.

If none of these facilities are used, however, the .gms and .gmi files could be identical for the direct input case.

A built-in variant of this approach is always accessible as a support tool. The user can automatically generate the internal image of a .gmi file by invoking the template (t) mode of startup of GMS, in which case the system will walk the user through a template stored in a .gmt (genomic messaging template) file, requesting where new variable data is to be added (which is whenever characters ???? are encountered in the template file). The result is subject to the above transformations which normally occur when a .gmi file is converted to a .gms file.

In many cases it is more convenient to think of the .gmi file as the clinical context to which genomic data will be added. In such cases, the genomic data, represented as DNA sequences with optional GMS commands and data included, is taken from a .gmd (genomic messaging dna) file.

The clinical data input file provides the skeleton structure into which the annotated genomic data will be merged. In a preferred embodiment, the clinical input data is CDA compliant, although GMS could accept any text file. The CDA file structure can be complex. For the purpose of GMS, only the basic features are important, and will be described here.

The CDA clinical input file can be, for example, a well-formed XML document. The root element corresponds to the "level" of CDA compliance. CDA <levelone> is the least restrictive, <levelthree> is the most restrictive. Within the CDA document is exactly one <clinical_document_header> and exactly one <body>. The header structure is specified in very deep detail by CDA, but for current GMS purposes, it serves primarily to identify the patient, and is processed essentially verbatim. The body structure is more flexible than the header. It contains the clinical content expressed using a small number of CDA-defined structures. GMS merges the genomic data into the body using these same structures. Shown below is an example of a clinical data input file, showing only the outermost XML structures for use with the current prototype. An example of a clinical CDA file for a bone marrow transplant case is shown in its entirety in Example 1.

```
<levelone>
    <clinical_document_header>
        <!--header structures per CDA-->
    </clinical_document_header>
    <body>
        <!--clinical content per CDA-->
        <!--GMS merges genomic data here-->
    </body>
</levelone>
```

System cartridges or downstream applications can add clinical and genomic annotation based on the availability of the combined clinical-genomic context.

The genomic data input file (.gmd) contains the DNA sequences and optional manual annotation. The DNA sequences are strings of bases. White space is ignored. The annotation is inserted using XML-style tags with a "gms" prefix, but the file is not an XML document. An example of a genomic input file is shown in Example 2.

"Cartridges" as used herein are replaceable program modules which transform input and output in various specialist ways. They may be considered as mini "Expert Systems" in the sense that they script expertise, customizations and preferences. All input cartridges ultimately generate .gms files as the final and main input step. This file is converted to a binary .gmb file and stored or transmitted. Input cartridges include, for example, Legacy Conversion Cartridges, for conversion of legacy clinical and genomic data into GMS language.

When the .gmi file is a CDA document, as might be expected when retrieving data from a modem clinical repository, GMS needs to know how to convert the content, marked up with CDA tags, into the required canonical .gms form. This is accomplished using a GMS "cartridge." In this scenario representing the first GMS cartridge application supporting automation, the expert optionally modifies a file obtained in CDA format to include additional annotation and structure. Again, the template mode described above is available to help guide this process so that the whole modified document remains CDA compliant. The resulting CDA document with added genomic features represents a "CDA Genomics Document." Such a CDA document can now be automatically converted into GMSL. In addition to the legacy record conversion cartridge described above, automatic addition of genomic data is also contemplated by the invention so that the CDA Genomics Document is itself automatically generated from the initial CDA genomics-free file.

For example, genomic data can be merged using a gms: namespace prefix at the end of the CDA <body>, in its own CDA <section> as shown below using CDA structure:

```
<cda:clinical_document_header>
    .
    .<!---header structures per CDA-->
    .
</cda:clinical_document_header>
<cda:body>
    .
    .<!--clinical sections per CDA-->
    .
    <cda:section>
        <cda:caption>
            IBM Genomic Messaging System Data
        </cda:caption>
        <cda:paragraph>
            <cda:content>
                <cda:local_markup ignore="markup">
                    <!--gms: tags go here-->
                </cda:local_markup>
            </cda:content>
        </cda:paragraph>
    </cda:section>
</cda:body>
```

More precisely, the cartridge looks first to see if the tags in bold already exist in the document, in which case it will keep them and insert there. If they are missing, it will look for a <gms:body or <body tag (case-insensitively). If however there is no body tag, it will insert the above before the last tag in the document.

The result of using the CDA conversion cartridge to merge clinical and genomic data is a .gms file in which all input is written in its canonical GMS form. Example 3 shows the .gms file produced by applying the cartridge to files shown in Examples 1 and 2. The GMS commands and syntax elements have been automatically generated and correctly inserted for processing by the GMS encoder.

V. Output

The incoming stream is processed byte by byte by the decoding GMS program and activity at the receiving device is determined by the data as it arrives. This includes activation of any embedded information, such as Perl applets. Passwords can be automatically requested at various points to allow the stream to proceed, and to unlock and read in data from any files available at the receiving end. These passwords can be distinct from and in addition to those mentioned above. Their locations in the stream can be chosen, for example, by the encoding expert or automatically by a legacy record conversion cartridge.

The system can generate standard outputs after receipt of incoming data. Examples of such standard outputs include, but are not limited to, a full report, an XML stream, an HTML stream, or a default viewer. These outputs represent various levels of fallback should other display or conversion systems fail. Additional outputs may be created by automated analysis cartridges.

The full report can include a file reports.dat, which displays and interprets the entire stream with interspersed notes on any errors or warnings, and with summaries of the DNA and all other data transmitted. A scan of this file for occurrences of the word "error" can be an efficient way to use this file for debugging of GMSL.

The file stream.xml includes the data stream and any annotation re-expressed in XML format. This is the primary file for use by downstream applications. Any CDA and even XML compliance of this file is, however, subject to correct preparation of the input file(s). A fast "psuedo send" and "pseudo-recieve" mechanism can provide the preparer the opportunity to test her/his entries. This mechanism can always be active in encoding the GMS stream—testing every message by a locally-confined "sending and receiving" process. Of various forms of output file, the most relevant at this time is CDA XML, which can be rendered at a GUI by various standard applications, such as XSL stylesheets. Hence, if the original input were a CDA XML file, the output could reproduce the original CDA input save for the DNA and annotation added by the expert to the original CDA clinical document.

The file stream.html includes an HTML display generated from stream.xml. It does not require the XML to be well formed. The opening tags can be transformed to a readable index on which the receiver can click to go to the content associated with that tag.

The default viewer can include a basic user interface (UI) which acts as a read-only editor text automatically invoked on receiving the GMS stream. The UI allows interrogation of the data on the stream.xml file, and follows the same indexing principle as the HTML output. It does not require the XML to be well formed. Although interpretation of the HTML is even more basic than in the XML output, it does include a regular-expression search string facility as well as standard backward-forward navigation. If it is not required, entering "quit" immediately escapes the editor.

One example of an automated analysis cartridge output is one that generates a protein sequence based upon the input data stream. A stream.seq file can be automatically generated by the protein analysis cartridge. The file can contain, for example, the protein sequence in all frame shift interpretations of the DNA, in FASTA format.

Automatic cartridges (replaceable code modules) are available both for processing input and output in different ways. They can be thought of as mini "Expert Systems" tailoring input and output for special purposes.

An especially powerful feature of the GMS system is the ability to analyze a decoded stream and augment that stream with the results of the analysis. Again, GMS cartridges can be used on output to perform these functions. Different cartridges (replaceable code modules) can be called into play depending on the intended use of the final output.

For example, cartridges of a type which do not alter the basic information, but affect display or presentation to physicians, administrators, and different health experts can be utilized. In the research context, for example, cartridges can add automatic annotation to the DNA of the patient, translate the DNA into protein sequences, and automatically annotate the proteins, while preserving and interlacing (if required) any manual annotation present in the original input. For diagnostic and vaccine development, for example, the cartridge can consider both pathogen and patient DNA. Example 4 shows the XML output after decoding and analyzing the stream produced from the .gms file in Example 3. Note the considerable expansion over the original DNA input file in Example 2.

VI. GMS Language Commands

A .gms file comprises a field of base pair characters, e.g., AGCT for DNA, in which commands are embedded. Some commands called data commands are followed by data and delimiters which indicate where that data begins and ends. They isolate important bioinformatic and clinical annotation from the surrounding field. Otherwise, all data is assumed to be DNA or commands related to DNA stream management, delimited by semicolon ';' or newline (\n, linefeed, carriage return). Spaces (whitespaces) are ignored, although if commands consist of multiple words, at least one should occur between the words.

The GMS language script can be generated on a .gms input file, which is the final input to GMS. The default root name for this and other files is assumed to be "stream" throughout. Hence the .gms file is stream.gms. The major stream information is then stream.gmb, the binary stream or file which can be encrypted and/or further compressed by the GMS program. In what follows, all data is written to stream.gms, and some (specified by index, comment, and bracket commands) will also be written to stream.gmb, the binary messaging stream. File stream.xml is generated on receipt and decoding (however an equivalent file is also generated on encoding and is compared as a check prior to sending). The following are exemplary GMS language commands.

| Most used example phrases and recipes | |
|---|---|
| password;[{identifier}{by my secret word protect data}] | Preferred first line on .gms file. For security the first data statement string must somewhere contain an encrypted identifier. It may be automatically substituted in the data statement by {identifier}. The first data statement will typically be a password data statement and ask for password too, checking it against the "password" specified, here the string "my secret word". |
| data;\Main security check-password required\ password;[Patient #1 {by shaman protect data}] | Use of data statement as message in subsequent passwords. "Main security check-password required" is shown at screen when program halts for password. |
| data;\<gene ID=LA:HLA00664 801 bp's, transplantation example>\;index; xml [<my_tag feature="asian polymorphism" locus="{locus}", sequence="{sequence}",/>\]; index;and protein | Writing a user-provided xml tag to stream.xml. Writing an xml tag to stream.xml with standard GMS variables, inserting it into the DNA sequence at that point and at the corresponding point in the protein translation. |
| data;[testing testing{employ data}] xml;[<test>{data}</test>{end of data}];index | Define the multipurpose GMS variable {data} as the string "testing testing" to write it in xml tags <test> to stream.xml (can be reused) |
| name;[my_tag\]; xml;[<scrubbed_data example="1"/>{define data}] name;[my_tag\]; xml;[{recall data}] | Defining xml tags or other data for reuse, here stored in a variable called "my_tag" |
| name;[mary\];xml;[elizabeth {define data}] xml;[<test> patient {identifier} has informal code name {mary}</test>\];index | Define the user variable {mary} as the string "elizabeth" for future use in data statements. Invoke GMS variable contairnng patient identifier. Write to stream.gmb and stream.xml |

-continued

| Most used example phrases and recipes | |
|---|---|
| hl7;\<hl7 bracket="{bracket}" level = "{level}"><br>MSH\|^~\&\|XRAY\|\|CDB\|\|\|\|ORU^R01\|K172\|P<cr><br>PID\|\|\|PATID1234^5^M11\|\|JONES^WILLIAM\|\|196106<br>13\|M<cr><br>OBR\|\|P8754^OE\|^XR1501^XR\|71020^Chest X-ray<br>PA\|\|198703281530\|198703290800<cr><br>OBX\|1\|TX\|71020\|\|It is a normal PA Chest X-ray\|\|\|\|\|F<cr><br></hl7>{end of data}];index | Writing hl7 in an XML context to stream.xml. Example use of variables, here {bracket} {level} reporting current status of ')' and '(' bracketing commands (see below). |
| dicom;[dfufhh7754D 432456F543%% . . .<br>. . . {end of very long terminator}] | Send image data in stream.gmb with terminator defined at start of use of GMS, unlikely to be encountered in long compressed streams (a priori probability is estimated). |
| perl;\<br>print "Perl applet test OK\n";print "Hit return:";<br><STDIN>;{applet data} | Sending a Perl applet in the stream.gmb. Activates when encountered. |
| A C G; G G; T; deletion; snp G<br>AAAAGGCGCGTTAGCCCC; | Place stream of DNA in stream.gmb and stream.xml. Put ACG in one byte, GG in one byte, T in one byte, record snp deletion at next point, record snp G at next point, pack rest as much as possible three per byte. |
| filedata;[{by shaman unlock data}]<br>number;[15 base pairs\]<br>squeeze dna<br>*<br>AGCTTCAGAGCTGCT\ | Compressing DNA four base pairs per byte (one base pair per two bits), and writing it to stream.gmb and stream.xml. Password, here "shaman", must have been entered by last used password command. |
| filedata;[template1.gms{by my secret word unlock data}]; read in dna | As above but read DNA (with * and \) from file specified (template1.gms) on receipt. Padlock file. Password, here "my secret word" must have been entered by an last used password command. |
| 01001011; | Research version only: write the byte corresponding to this binary |

| Commands which insert DNA into current sequence | |
|---|---|
| singlet X | Place X (AGC or T) as next current sequence and store 1 per byte in stream.gmb |
| X; | Place X (AGC or T) as next current sequence and store 1 per byte in stream.gmb |
| doublet X | Place XX (AGC or T) as next current sequence and store 2 per byte in stream.gmb |
| XX | Place XX (AGC or T) as next current sequence and store 2 per byte in stream.gmb. |
| triplet XXX | Place XXX (AGC or T) as next current sequence and store 3 per byte in stream.gmb. |
| XXX | Place XXX (AGC or T) as next current sequence and store 3 per byte in stream.gmb. |
| snp X | Place X (AGC or T) as next current sequence and record as a single nucleotide polymorphism, and store as 1 per byte in stream.gmb. |
| XXXXXXXXXXXXXX | Pack as much as possible into triplets (i.e. 3 per byte) in stream.gmb. Stragglers modulo 3 are put into singlets or doublets. |

| General commands (no arguments; DNA annotation and validation checks) | |
|---|---|
| insertion ( | Place marker in stream.gmb that DNA begins here. |
| ) insertion | Place marker in stream.gmb that DNA insertion end here. |
| deletion | Place marker in stream that DNA deletion occurs here. |
| end of task | Terminate whole task. Ignore following information. |
| index | Write content of last data statement (usually an xml data statement) on stream.xml. |
| and protein | Qualify last used index statement to write content of last data statement on stream.xml and reproduce at same location in the translated protein sequences reported on stream.xml. Viz:- index; and protein; |
| (escape character) | Required for internal working of GMS. Also, ensure data termination if content of a preceding data statement abnormally skipped. |
| ] | Perform parity check on last data statement Also the optional post-terminator symbol, see below. |
| [ | No action in Version 00. Useful in conjunction with ']' to bracket sets of commands and data in the stream. Also an initiator symbol (see below) if follows data command such as data, viz:- data;[ |
| danger | Flag a warning. 00000000 coding this command should no be encountered in normal mode. |
| validate | Advance validation counter 1 |

| Commands which write xml (to stream.xml) | |
|---|---|
| comment | Write to stream.xml:<br><![CDATA[<gms:comment type="{bracket}" state="{state}" type="{type}" level="{level}"\"><br>contents of previous data statement<br></gms:comment>]]> |
| new dna | Write to stream.xml<br><gms:automated_annotation><br><gms:dna sequence="{sequence}" base="{base}" locus="{locus}"><br>Here: all annotation tags added manually plus all added automatically, including automatic translation and protein annotation. </gms:dna><br><gms:dna sequence="{sequence}" base="{base}" locus="{locus}">.<br>Used first time, sets sequence count to 1. If used again, advances the sequence counter to indicate new sequence and writes |
| end of dna | Add special end null entry, and properly close 'new dna' annotation tags on stream.xml.<br>{end}</gms:dna><br><gms:dna_checks><br>summary data<br></gms:dna_checks><br><gms:automated_annotation> |

-continued

| Commands which write xml (to stream.xml) | |
|---|---|
| (n<br>e.g. (63 | Write an self-standing xml annotation tag to stream.xml<br><gms:open feature="text" type="n" level="level"/><br>where text is the content the last data statement, n is the bracketing type n, and level is the bracketing level for this type. n may be 0 . . . 63 |
| )n<br>e.g.)63 | Write an self-standing xml annotation tag to stream.xml<br><gms:close feature="text" type="n" level="level"\><br>where text is the content of the last data statement, n the bracketing type n, and level is the bracketing level for this type. n may be 0 . . . 63 |

A data statement includes the data command followed by initiator symbol or symbols, the stream of data which will be encoded one byte per character, and the terminator symbol or symbols. An example of a data command format is Data_command, delimiter, initiator, . . . data . . . , terminator[optional post terminator command], where the semicolon or newline character is required as the usual delimiter for commands (and commas above are for clarity and do not appear in actual use).

Note that, as with the delimitation of all commands, the semicolon can be omitted and replaced by the newline character ('\n', "carriage return", "linefeed"), and interspersed whitespace is not significant. An example appearance of a data statement is:

data

\my list of data\

For security, the first data statement, but not necessarily the first information, on the .gmi file, has a special status. It is typically a password statement which is a special case of a data statement as described below. Comment may be added around {identifier} and within the enclosing square brackets, but not after the {by my_password protect data} statement. There are two implied passwords—that implied by {identifier} at that by my_password. "my_password" is any other word or phrase (a word like Mary would do equally well) selected by the preparer of the .gmi file, and must be entered by the receiver on receipt when requested. The password "{identifier}" must be satisfied even before the decoded stream gets as far as asking for the above password. The string as written in the .gmi file is either exactly that string "{identifier}" of 2 curly brackets and 10 alphabetic letters, or alternatively, a string identical to that generated by the encrypted form of "Enter Identifier" request above, e.g. 01gC/VymltaB. In effect {identifier} is the variable which automatically inserts the string e.g. 01gC/VymltaB into the password statement.

The command data in the above example is an example of a specific data command amongst several other possible specific data commands, and they collectively represent generic or general data commands. Examples of such commands are set forth below. Those in brackets below perform no further supported function in version 00 but are acceptable as general data.

| Data commands (arguments following in [ . . . data}] or sometimes \ . . . \, or [ . . . \]) | | | |
|---|---|---|---|
| Data command | Assumed data content | Special action | Termination. Use \ or escape character as data terminator, or may \ appear as content? |
| data | Any data. | None. | \ terminator or {end of data}. If terminated by {employ data}, this data will substitute the string {data} in any subsequent data statement. If terminated by {store data}, it will substitute for {name} where name is the contents of previous data statement. |
| perl | Executable Perl | If terminated by {applet data}, automatically runs applet. | Usually {applet data}. Not executed on {end of data} |
| dna | DNA data to be stored 'classically' as the ASCII characters AGCT including new characters | None, except to prevent this data from being inserted into current dna sequence. Instead it can be stored in a variable name using {store data} (see 'data' above) | \ terminator or {end of data} |
| squeeze dna | DNA to compress 2 bits per bp, viz:- number;[5 base pairs\];squeeze dna; * AGCTC \ | Add to current dna sequence and squeezes into 4 bp's per byte as much as possible. Stragglers left modulo 4 are stored as singlet, doublet or triplet commands | Termination controlled by number in previous data statement but '\' should be present as check. |
| read in dna | As squeeze dna, but gets data from file, viz:- filedata;[template1.gms {by shaman unlock data}] | As squeeze dna. | As squeeze dna, but end of file condition terminates too. |
| number | Any integer embedded in text up to decimal point. | Data ignored (deleted) after decimal point '.'. | \ terminator or {end of data}. {store data} and {employ data} also useful. |
| xml | Any valid part of XML compliant document | None | \ terminator or {end of data}. {store data} and {employ data} also useful. |
| hl7 | Any HL7 | None | Content only. use {end of data} |
| dicom | DICOM data | None | Content only. use {end of data}. For large amounts of data, redefine end-of-data at startup (this calculates for the user the probability of chance occurrence. |

-continued

Data commands (arguments following in [ ... data}] or sometimes \ ... \, or [ ... \])

| Data command | Assumed data content | Special action | Termination. Use \ or escape character as data terminator, or may \ appear as content? |
|---|---|---|---|
| base pairs | As command dna, but normally used to add annotation referring to short segments | None, except to distinguish it from command 'dna' above and also from dna to be inserted into current dna sequence. | \ terminator or {end of data}. {store data} and {employ data} also useful. |
| protein | Protein data to be stored 'classically' as the ASCII characters GAVLIST ... Including new characters | None | \ terminator or {end of data}. {store data} and {employ data} also useful. |
| filedata | File name or other file instructions, e.g.. filedata;[template1.gms {by password unlock data}];read in data | Report possible need for password, in run record. If text data is present, defines active external file as other than template.gmb. If {by password unlock data} is the data terminator, the last entered password is required to continue. | Usually {on password unlock data}. \ terminator valid if no password check required to continue. |
| password | Any text. Not used as password, but text may be comment or used later as it would be by any data statement | Halts screen and request password. If data terminates with {on password protect data} compare string password with entry, otherwise keep till it check requested. | Usually {on password protect data}. \terminator is valid and password becomes last password entered, but check is not done at that time. |
| instruction | Reserved for extended instruction set | Switch instruction mode. | Usually \ terminator, or {end of data} |
| name | General name for something | None | Usually \ terminator, or {end of data} |
| xml cdata | As xml but preferred for use for cdata intensive data | None | Usually \ terminator, or {end of data} |
| conditional | Conditional action, not implemented | Perform condition/logic test | Usually \ terminator, or {end of data} |
| skip | Number of bytes to skip if number, to or label to skip to if last condition tested is true. Not implemented. | Perform skip. | Usually \ terminator, or {end of data} |
| label | Data is label for reference. | None | \ terminator or {end of data}. {store data} and {employ data} also useful. |

In the example data;\my list of data\, the first backslash represents the initiator and the second the terminator. Possible initiators include:

| Initiator commands | |
|---|---|
| \ | Read data till terminator or end of file is encountered. |
| [ | Read data till terminator or end of file is encountered. Usually used for style in conjunction with character ] described below. |
| *n | Read following n characters where n is 1–255 or end of file is encountered. e.g *100. Usually first non-comment '#' line when data is on background file. |
| * | Read following N characters where N is the numeric value in the preceding data statement or end of file is encountered. Usually first non-comment '#' line when data is on background file, in which case the preceding data statement is in the main .gmb file. |

| Terminator commands | |
|---|---|
| escape character (appears as backarrow on screen) | Terminate data except for perl, hl7, dicom data types (which may use this character. |
| end of file | Terminates any data stream being read on main or background file. |
| \ (i.e. backslash) | On reading GMS file, replace by escape character as above. |
| {end of data} | Terminate data of any type. This and other 'data}' commands (note whitespace) below collectively provide less than a one in a $256^{12}$ a priori probability of chance encounter of characters which will inadvertently prematurely terminate a stream. |
| {end of terminatorstring} | When specified at startup of encoding, all terminator commands ending 'data}' (note whitespace) are inactivated and replaced by corresponding terminatorstring} commands |
| {applet data} | Terminate data of any type and immediately attempt to execute data assuming it to be Perl script. |
| {define data} | Terminate data of any type and store under the name name defined by the data in the preceding data statement. Also, create general substitution variable {name} storing that data. |
| {recall data} | Terminate data of any type and replace all of that data, if any, by data stored under the name defined by the preceding data statement. |
| {employ data} | Terminate data of any type and store data as a string in the specific internal variable called KEEPDATA. |
| {deploy data} | Terminate data of any type and replace any and all occurrences of string '{data}' in that data by the string stored in the specific internal variable called KEEPDATA. |
| {by password protect data} | Terminate data of any type and abort if current active password does not match password specified. |
| {by password unlock data} | Terminate data of any type and abort if current active password does not match password specified. If it does match, the data is interpreted as the name of an external file to be opened and the suffix .gmb is added. If the suffix .gmb or .gms |

| Terminator commands | |
|---|---|
| | is already represented in the filename, suffix .gmb is assumed. If the data is empty the standard root filename is assumed. |

If the string 'data}' is encountered and the terminator is not one of the above terminator commands ending in 'data}', the error "unidentified terminator qualifier construct" is reported and GMS decoding aborts.

| Optional post-terminator symbols | |
|---|---|
| ] | Perform parity check on data. In effect, calculate ]0 or ]1 to send in stream as below. |
| ]0 | Parity must be even, abort otherwise |
| ]1 | Parity must be odd, abort otherwise |

Substitution variable commands can appear anywhere in a data statement. They are replaced by a current value of a corresponding variable in the GMS program.

| Substitution variable commands | |
|---|---|
| {version} | Current version of GMS system used to encode. If this variable is used, it must match decode version used or GMS aborts on decoding. |
| {identifier} | Current patient identifier entered in startup of encoding, or, if the "scrub" mode is set at that time, its encrypted form. The string '{identifier}' can be used throughout the initial .gmi input file (not just in data statements) and is assigned only on initiation of encoding. If it is not matched on decoding, GMS decoding aborts. |
| {id} | Current patient identifier encrypted or not according to whether the scrub mode is set or not. |
| {open id} | The unscrubbed identifier |
| {closed id} | The scrubbed identifier |
| {scrub status} | 1 is scrubbing is set, 0 otherwise |
| {density} | Very roughly, chances of recognizing just one word after encryption has taken place. |
| {point} | Current command byte being decoded. Useful in indexing to the raw GMS binary stream. |
| {xml symbols} . . . {end xml symbols} | Replace all intervening non-xml symbols by their standard XML protected & 'ampersand' forms. |
| . . . {treat as peptide} | Convert all preceding part of data to formally correct definition of peptide or protein sequence, and add automatic annotation (if cartridge is present). |
| {sequence} | Current DNA sequence number |
| {locus} | Current base pair number in that sequence |
| {base} | Current accumulative base pair count over all sequences (i.e., not reset per sequence). |
| {data} | Current string stored in internal KEEPDATA variable |
| (sourcefile} | Current main sourcefile root name (default 'stream') |
| {backgroundfile} | Current background or 'template' file root name specified by filedata command |
| {bracket} | The last type of GMS bracket used e.g. )2 |
| {level} | The bracket level of the last type of GMS bracket used e.g. )2 |

-continued

| Substitution variable commands | |
|---|---|
| {state} | The state 'open' or 'closed' of the last type of GMS bracket used. |
| {name} | The string stored in the variable name defined by any earlier {define data} terminator |

Although illustrative embodiments of the present invention have been described herein, it is to be understood that the invention is not limited to those precise embodiments, and that various other changes and modifications may be effected therein by one skilled in the art without departing from the scope or spirit of the invention. The following examples are provided to illustrate the scope and spirit of the present invention. Because these examples are given for illustrative purposes only, the invention embodied therein should not be limited thereto.

EXAMPLE 1

CDA .gmi File

The following example shows a clinical CDA file for an anonymous bone marrow transplant case. The clinical CDA information has been written to a CDA.gmi file as described above.

```
<?xml version="1.0" encoding="UTF-8"?>
<!--Sample XML file generated by XML Spy v4.0.1 U
(http://www.xmlspy.com)-->
<leveltwo xmlns:gms="GMS_schemas" xmlns:bmt="BMT_schemas"
xmlns:cda="KAI_CDA"
xmlns:xsi="http://www.w3.org/2001/XMLSchema-instance"
xsi:schemaLocation="BMT_schemas BMT_Discharge.xsd">
    <cda:clinical_document_header>
        <cda:id EX="BMT_1630" />
<!--Based on the spec "LOINC_Document_Names_Spreadsheet.xls" from
LOINC-->
        <cda:document_type_cd S="2.16.840.1.113883.6.1" DN="SE.Bone
Marrow" />
        <cda:origination_dttm V="2001-09-02" />
        <cda:confidentiality_cd ID="CONF1" V="N"
S="2.16.840.1.113883.5.10228" />
<!--
        <document_relationship>
            This document should have relationships with the
corresponding discharge note, more reports for this patient and possibly
            successive transplantations. The way to represent it is
not yet defined.
        </document_relationship>
-->
        <cda:patient_encounter>
            <cda:id EX="HDBMT1675" RT="2.16.840.1.113883.3.999" />
            <cda:practice_setting_cd V="BMTU" S="2.16.840.1.113883.5.10911"
DN="Bone marrow Transplant unit" />
            <cda:encounter_tmr V="1999-04-08 1999-05-20" />
            <cda:service_location>
                <cda:id EX="HDBMT107400" RT="2.16.840.1.113883.3.999" />
                <cda:addr>
                    <cda:STR V="Ein-Karem" />
                    <cda:CTY V="Jerusalem" />
                    <cda:STA V="Israel" />
                    <cda:ZIP V="91120" />
                </cda:addr>
            </cda:service_location>
        </cda:patient_encounter>
        <cda:legal_authenticator>
            <cda:legal_authenticator.type_cd V="SPV" />
            <cda:participation_tmr V="2001-09-02" />
            <cda:signature_cd V="S" />
            <cda:person>
                <cda:id EX="HD11" RT="2.16.840.1.113883.3.999" />
                <cda:person_name>
                    <cda:nm>
                        <cda:GIV V="Unknown" />
                        <cda:FAM V="Ben-Yosef" />
                        <cda:SFX V="MD" QUAL="PT" />
                    </cda:nm>
                    <cda:person_name.type_cd V="L"
S="2.16.840.1.113883.5.200" />
                </cda:person_name>
            </cda:person>
        </cda:legal_authenticator>
        <cda:originator>
            <cda:originator.type_cd V="AUT" />
            <cda:participation_tmr V="1999-06-20" />
```

-continued

```
            <cda:person>
                <cda:id EX="HD127" RT="2.16.840.1.113883.3.999" />
                <cda:person_name>
                    <cda:nm>
                        <cda:GIV V="Unknown" />
                        <cda:FAM V="Ben-Yosef" />
                        <cda:SFX V="MD" />
                    </cda:nm>
                    <cda:person_name.type_cd V="L"
S="2.16.840.1.113883.5.200" />
                </cda:person_name>
            </cda:person>
        </cda:originator>
        <cda:originating_organization>
            <cda:originating_organization.type_cd V="CST" />
            <cda:organization>
                <cda:id EX="HD" RT="2.16.840.1.113883.3.999" />
                <cda:organization.nm V="Hadassah University Hospital" />
            </cda:organization>
        </cda:originating_organization>
        <cda:provider>
            <cda:provider.type_cd V="PRF" />
            <cda:person>
                <cda:id EX="HD171" RT="2.16.840.1.113883.3.999" />
            </cda:person>
        </cda:provider>
        <cda:provider>
            <cda:provider.type_cd V="ASS" />
            <cda:person>
                <cda:id EX="HD2831" RT="2.16.840.1.113883.3.999" />
            </cda:person>
        </cda:provider>
        <cda:provider>
            <cda:provider.type_cd V="CON" />
            <cda:person>
                <cda:id EX="HD346" RT="2.16.840.1.113883.3.999" />
            </cda:person>
        </cda:provider>
        <cda:patient>
            <cda:patient.type_cd V="PATSBJ" />
            <cda:person>
                <cda:id EX="BMT1630" RT="2.16.840.1.113883.3.999" />
                <cda:person_name>
                    <cda:nm>
                        <cda:GIV V="Dana" />
                        <cda:FAM V="Newman" />
                    </cda:nm>
                </cda:person_name>
            <cda:person>
            <cda:birth_dttm V="1968-01-01" />
            <cda:administrative_gender_cd V="F" S="2.16.840.1.113883.5.1"
/>
        </cda:patient>
    </cda:clinical_document_header>
    <BMT_Discharge_Body>
        <General_Information>
            <UPN_IUMBID>String</UPN_IUMBID>
            <TransplantDate>1999-04-20</TransplantDate>
<ChronologicalTransplantNumber>0</ChronologicalTransplantNumber>
        </General_Information>
        <PreBMT>
            <Diagnoses>
                <SemiStructuredDescription>
                    <bmt:SpecificDiseaseCode>
                        <diseaseClassification>CML:
unspecified</diseaseClassification>
                    </bmt:SpecificDiseaseCode>
                    Suspected Rheumatoid Arthritis.</SemiStructuredDescription>
            </Diagnoses>
            <History>
                <cda:body>
                    <cda:section>
                        <cda:caption>
                            <cda:caption_cd V="10164-2" S="2.16.840.1.113883.6.1"
/>
```

-continued

```
                        History of Present Illness</cda:caption>
                        <cda:paragraph>
                                <cda:content>John Smith, a 31-year-old male has
suffered from over hyper hidrosis and Malaise Since September 1998. He
was diagnosed with CML with positive Philadelphia Chromosome. Treated
with Hydrea and Alluporinol. Two months later he developed small joint
arthritis and was diagnosed with Rheumatoid Arthritis. No known
sensitivities to drugs. No other known diseases.</cda:content>
                        </cda:paragraph>
                    </cda:section>
                </cda:body>
            </History>
            <Physical_Examination>
                <cda:body>
                    <cda:section>
                        <cda:caption>
                            <cda:caption_cd V="11384-5" S="2.16.840.1.113883.6.1"
/>
                        Physical Examination</cda:caption>
                        <cda:paragraph>
                                <cda:content>- In good condition in general, weight
69 Kg, height 178 cm, B.P 70/110, pulse 80 Normal rhythm, Temperature
36.2 c - Head, eyes and pharynx: without pathological findings - Lymph
nodes were not enlarged in all Stations - Lungs: vesicular breathing - -
Heart: normal sounds - Abdomen: Soft - Liver and spleen: without
pathological findings - Limbs: without pathological
findings</cda:content>
                        </cda:paragraph>
                    </cda:section>
                </cda:body>
            </Physical_Examination>
            <Lab_Data>
                <cda:body>
                    <cda:section>
                        <cda:caption>
                            <cda:caption_cd V="22032-7" S="2.16.840.1.113883.6.1"
/>
                        Lab Data</cda:caption>
                        <cda:paragraph>
                                <cda:content>- Hemoglobin: 13.1 gr% - Thrombocytes:
761k - Leukocytes: 4k - LDH: 1901 - Liver Function Tests (LFTs) : Normal
- CMV: Positive - HBSAG: Negative - HIV: Negative - Anti HCAS: Negative
- Blood Type: AB+ - CSF: Normal</cda:content>
                        </cda:paragraph>
                    </cda:section>
                </cda:body>
            </Lab_Data>
            <Known_Allergies>
                <cda:body>
                    <cda:section>
                        <cda:paragraph>
                            <cda:content>No known Allergies.</cda:content>
                        </cda:paragraph>
                    </cda:section>
                </cda:body>
            </Known_Allergies>
            <Conditioning>
                <cda:body>
                    <cda:section>
                        <cda:paragraph>
                            <cda:content>- Fludarabine: 33k mg / per day * 6
days - Busulfan: 550 mg/day * 2 days - ATG: 2800 mg /day * 4 days -
ARA-C Intra-thecal 50 mg</cda:content>
                        </cda:paragraph>
                    </cda:section>
                </cda:body>
            </Conditioning>
        </PreBMT>
        <BMT>
            <Donor>
                <cda:body>
                    <cda:section>
                        <cda:paragraph>
                            <cda:content>- Father, full match in HLA Typing -
CMV: borderline - HBSAG: Negative - HIV: Negative - Blood Type:
A+</cda:content>
                        </cda:paragraph>
                    </cda:section>
                </cda:body>
```

-continued

```
            </Donor>
            <Transplant>
                <SemiStructuredDescription>
                    <bmt:Graft>Allogeneic</bmt:Graft>
                    <bmt:StemCellsSource>
                        <PB>Peripheral blood</PB>
                    </bmt:StemCellsSource>
                    T-Cell Depletion with 0.35 ml Compath, cell quantity of 4.92
* 10^8 Cells/kg</SemiStructuredDescription>
            </Transplant>
        </BMT>
        <PostBMT>
            <cda:body>
                <cda:section>
                    <cda:caption>
                        <cda:caption_cd V="P1-67D40" S="2.16.840.1.113883.6.5" />
                        Transplantation Outcome</cda:caption>
                    <cda:paragraph>
                        <cda:content>- Thrombocytes were taken on the second
day after transplantation - The count of Thrombocytes was not less than
25k during the transplantation - Light decrease in Liver Enzymes up to
86-108TP and 56PT- P3 - PNN was given to treat ATG - Decrease in body
temperature with no infection found in blood - Treated with Cefuroxime
and Gentamicin and treatment stopped when blood counts returned to
normal - Unilateral left hemiparesis, resolved in a short time - CT was
normal as well as EEG for follow-up</cda:content>
                    </cda:paragraph>
                </cda:section>
            </cda:body>
        </PostBMT>
        <At_Discharge>
            <Situation_At_Discharge>
                <cda:body>
                    <cda:section>
                        <cda:caption>
                            <cda:caption_cd V="8652-0" S="2.16.840.1.113883.6.1"
/>
                            Status of Patient at Discharge</cda:caption>
                        <cda:paragraph>
                            <cda:content>Light rash which resolved
spontaneously without steroids. No GvHD was diagnosed.</cda:content>
                        </cda:paragraph>
                    </cda:section>
                    <cda:section>
                        <cda:caption>
                            <cda:caption_cd V="10183-2" S="2.16.840.1.113883.6.1"
/>
                            Medications at Discharge</cda:caption>
                        <cda:paragraph>
                            <cda:content>Losec 20 mg Acyclovir 800mg × 4/d CSA
200 mg × 2</cda:content>
                        </cda:paragraph>
                    </cda:section>
                </cda:body>
            </Situation_At_Discharge>
            <Discharge_Plans>
                <cda:body>
                    <cda:section>
                        <cda:caption>
                            <cda:caption_cd V="8653-8" S="2.16.840.1.113883.6.1"
/>
                            Instructions to Patient and Family</cda:caption>
                        <cda:paragraph>
                            <cda:content>Follow-up in our out-patient clinic on
coming Sunday.</cda:content>
                        </cda:paragraph>
                    </cda:section>
                </cda:body>
            </Discharge_Plans>
            <Instructions_To_Patient_And_Family>
                <cda:body>
                    <cda:section />
                </cda:body>
            </Instructions_To_Patient_And_Family>
        </At_Discharge>
    </BMT_Discharge_Body>
    <cda:section>
        <cda:caption>IBM Genomic Messaging System Data</cda:caption>
        <cda:paragraph>
```

```
        <cda:content>
            <cda:local_markup ignore="markup">
            </cda:local_markup>
        </cda:content>
    </cda:paragraph>
  </cda:section>
</leveltwo>
```

EXAMPLE 2

DNA .gmd File

The following example shows a genomic input file that can be utilized in accordance with an embodiment of the invention. The genomic input file contains the genomic sequence to be processed.

```
<gms:genomic_data>
<gms:gene sequence="HLA00664,DRB1*0101,801 bases, 80C9FCB6 checksum" />

<gms:t_cell_epitopes>
  <gms:protein>pkyvkqntlkla</gms:protein>

<gms:protein>gplkaeiaqrle</gms:protein>
</gms:t_cell_epitopes>

ATGGTGTGTC TGAAGCTCCC TGGAGGCTCC TGCATGACAG CGCTGACAGT GACACTGATG

GTGCTGAGCT CCCCACTGGC TTTGGCTGGG

<gms:experimental_start_of_mature_peptide />

GAC ACCCGAC CACGTTTCTT GTGGCAGCTT AAGTTTGAAT GTCATTTCTT CAATGGGACG

GAGCGGGTGC GGTTGCTGGA AAGATGCATC TATAACCAAG AGGAGTCCGT GCGCTTCGAC

AGCGACGTG

<gms:snp>G GG
<gms:annotation>allotype is g in drb1*0101, r in
drb1*0105</gms:annotation>
</gms:snp>

GAGTACCGGGCGGTGACG GAGCTGGGGC GGCCTGATGC CGAGTACTGG AACAGCCAGA

AGGACCTCCT GGAGCAGAGG CGGGCCGCGG TGGACACCTA CTGCAGACAC AACTACGGGG

TTGGTGAGAG CTTCACAGTG CAGCGGCGAG TTGAGCCAA GGTGACTGTG TATCCTTCAA

AGACCCAGCC CCTGCAGCAC CACAACCTCC TGGTCTGCTC TGTGAGTGGT TTCTATCCAG

GCAGCATTGA AGTCAGGTGG TTCCGGAACG GCCAGGAAGA GAAGGCTGGG GTGGTGTCCA

CAGGCCTGAT CCAGAATGGA GATTGGACCT TCCAGACCCT GGTGATGCTG GAAACAGTTC

CTCGGAGTGG AGAGGTTTAC ACCTGCCAAG TGGAGCACCC AAGTGTGACG AGCCCTCTCA

CAGTGGAATG GAGAGCACGG TCTGAATCTG CACAGAGCAA GATGCTGAGT GGAGTCGGGG

GCTTCGTGCT GGGCCTGCTC TTCCTTGGGG CCGGGCTGTT CATCTACTTC AGGAATCAGA

AAGGACACTC TGGACTTCAG CCAACAGGAT TCCTGAGCTG A

<gms:new_fragment>
<gms:annotation>possible somatic mutation cell line #4
end-11th</gms:annotation>

AGGAATCAGA AAGGACACTC TGGACTTCAG CCAACAGGAT ACCTGAGCTG

A</gms:new_fragment>
</gms:genomic_data>
```

EXAMPLE 3

.gms File from CDA Cartridge (Header and Clinical Sections Removed)

This example shows a .gms file obtained from a CDA cartride in accordance with an embodiment of the invention. The .gms file was produced by applying a CDA conversion cartidge to merge the clinical data shown in Example 1 with the genomic data set forth in Example 2.

```
<?xml version="1.0" encoding="UTF-8"?>
<!--Sample XML file generated by XML Spy v4.0.1 U
(http://www.xmlspy.com)-->
<leveltwo xmlns:gms="GMS_schemas" xmlns:bmt="BMT_schemas"
xmlns:cda="KAI_CDA"
xmlns:xsi="http://www.w3.org/2001/XMLSchema-instance"
xsi:schemaLocation="BMT_schemas BMT_Discharge.xsd">
  <cda:clinical_document_header>
  </cda:clinical_document_header>

<cda:section>
     <cda:caption>IBM Genomic Messaging System Data</cda:caption>

<cda:paragraph>
        <cda:content>
           <cda:local_markup ignore="markup">{end of data}];index;
xml;[
           <gms:annotation>{xml symbols} GMS-augmented document created
Sat Dec 1 17:25:59 2001 gms:environment tags allow use of valid xml as
annotation mixed with DNA in ..GATTACCA.. format, and executable GMSL
(Genomic Messaging Stream Language) as content. The GMSL will activate
immediately when program gms is run with the IBM-Yorktown legacy
conversion cartridge option selected for IBM-Haifa CDA hospital files.
{end xml symbols}</gms:annotation>

{end of data}];index; xml; [
           <gms:genomic_data>{end of data}];index;new dna xml; [
           <gms:gene sequence="HLA00664,DRB1*0101,801 bases, 80C9FCB6
checksum" />

{end of data}];index;and protein xml; [
           <gms:t_cell_epitopes>{end of data}];index;and protein xml; [
           <gms:protein>{end of data}];index;and protein;protein; [
pkyvkqntlkla {treat as peptide}\];index;and protein;xml; [</gms:protein>

{end of data}];index;and protein; xml; [
           <gms:protein>{end of data}];index;and protein;protein; [
gplkaeiaqrle {treat as peptide}\];index;and protein;xml; [</gms:protein>

{end of data}];index;and protein;
xml; [</gms:t_cell_epitopes>

{end of data}];index;and protein ATGGTGTGTC TGAAGCTCCC
TGGAGGCTCC TGCATGACAG CGCTGACAGT GACACTGATG GTGCTGAGCT CCCCACTGGC
TTTGGCTGGG xml; [

<gms:experimental_start_of_mature_peptide />
           {end of data}];index;and protein GAC ACCCGAC CACGTTTCTT
GTGGCAGCTT AAGTTTGAAT GTCATTTCTT CAATGGGACG GAGCGGGTGC GGTTGCTGGA
AAGATGCATC TATAACCAAG AGGAGTCCGT GCGCTTCGAC AGCGACGTG xml; [

<gms:snp>{end of data}];index;and protein G GG xml; [
           <gms:annotation>{xml symbols} allotype is g in drb1*0101, r
in drb1*0105 {end xml symbols}</gms:annotation>

{end of data}];index; xml; [</gms:snp>

{end of data}]; index; and protein GAGTACCGGCGGTGACG
GAGCTGGGGC GGCCTGATGC CGAGTACTGG AACAGCCAGA AGGACCTCCT GGAGCAGAGG
CGGGCCGCGG TGGACACCTA CTGCAGACAC AACTACGGGG TTGGTGAGAG CTTCACAGTG
```

-continued

```
CAGCGGCGAG TTGAGCCTAA GGTGACTGTG TATCCTTCAA AGACCCAGCC CCTGCAGCAC

CACAACCTCC TGGTCTGCTC TGTGAGTGGT TTCTATCCAG GCAGCATTGA AGTCAGGTGG

TTCCGGAACG GCCAGGAAGA GAAGGCTGGG GTGGTGTCCA CAGGCCTGAT CCAGAATGGA

GATTGGACCT TCCAGACCCT GGTGATGCTG GAAACAGTTC CTCGGAGTGG AGAGGTTTAC

ACCTGCCAAG TGGAGCACCC AAGTGTGACG AGCCCTCTCA CAGTGGAATG GAGAGCACGG

TCTGAATCTG CACAGAGCAA GATGCTGAGT GGAGTCGGGG GCTTCGTGCT GGGCCTGCTC

TTCCTTGGGG CCGGGCTGTT CATCTACTTC AGGAATCAGA AAGGACACTC TGGACTTCAG

CCAACAGGAT TCCTGAGCTG A new dna xml; [

<gms:annotation>{xml symbols} possible somatic mutation cell
line #4 end-11th {end xml symbols}</gms:annotation>

{end of data}];index; AGGAATCAGA AAGGACACTC TGGACTTCAG

CCAACAGGAT ACCTGAGCTG A end of dna xml; [</gms:genomic_data>

\];index; xml;[</cda:local_markup>
        </cda:content>
      </cda:paragraph>
    </cda:section>
</leveltwo>
```

EXAMPLE 4

.xml File after Automatic Annotation (Header and Clinical Sections Removed)

This example shows the XML output in accordance with an embodiment of the invention after decoding and analyzing the stream produced from the .gms file in Example 3. The output shown below incorporates annotation incorporates annotation of the genomic sequences as well as protein annotation.

```
<?xml version="1.0" encoding="UTF-8"?>
<!--Sample XML file generated by XML Spy v4.0.1 U
(http://www.xmlspy.com)-->
<leveltwo xmlns:gms="GMS_schemas" xmlns:bmt="BMT_schemas"
xmlns:cda="KAI_CDA"
xmlns:xsi="http://www.w3.org/2001/XMLSchema-instance"
xsi:schemaLocation="BMT_schemas BMT_Discharge.xsd">
  <cda:clinical_document_header>
  </cda:clinical_document_header>

<cda:section>
    <cda:caption>IBM Genomic Messaging System Data</cda:caption>

<cda:paragraph>
      <cda:content>
          <cda:local_markup ignore="markup">
            <gms:annotation>GMS-augmented document created Sat Dec. 1
17:25:59 2001 gms:environment tags allow use of valid xml as annotation
mixed with DNA in ..GATTACCA.. format, and executable GMSL (Genomic
Messaging Stream Language) as content. The GMSL will activate
immediately when program gms is run with the IBM-Yorktown legacy
conversion cartridge option selected for IBM-Haifa CDA hospital
files.</gms:annotation>

<gms:genomic_data>
              <gms:dna sequence="1" base="1" locus="1">
              <gms:gene sequence="HLA00664,DRB1*0101, 801 bases,
80C9FCB6 checksum" />

<gms:t_cell_epitopes>
                <gms:protein>pkyvkqn
```

```
                                -continued
<gms:pkc_phosphorylation>tlk</gms:pkc_phosphorylation> la
          <gms:protein_feature type="whole_sequence"
sequence="1" context="binding peptide?" readingframe="3 complement"
start="1" stop="12" />

<gms:protein_feature type="pkc_phosphorylation"
sequence="1" readingframe="3 complement" start="8" stop="10" />
        </gms:protein>

<gms:protein>gplkaeiaqrle
          <gms:protein_feature type="whole_sequence"
sequence="1" context="binding peptide?" readingframe="3 complement"
start="1" stop="12" />
        </gms:protein>
      </gms:t_cell_epitopes>
ATGGTGTCTGAAGCTCCCTGGAGGCTCCTGCATGACAGCGCTGACAGTGACACTGATGGTGCTGAGCTCC

CCACTGGCTTTGGCTGGG

<gms:experimental_start_of_mature_peptide />

GACACCCGACCACGTTTCTTGTGGCAGCTTAAGTTTGAATGTCATTTCTTCAATGGGACGGAGCGGGTGCGG

TTGCTGGAAAGATGCATCTATAACCAAGAGGAGTCCGTGCGCTTCGACAGCGACGTG

<gms:snp>GGG
          <gms:annotation>allotype is g in drb1*0101, r in
drb1*0105</gms:annotation>
          </gms:snp>

GAGTACCGGGCGGTGACGGAGCTGGGGCGGCCTGATGCCGAGTACTGGAACAGCCAGAAGGACCTCCTGGAG

CAGAGGCGGGCCGCGGTGGACACCTACTGCAGACACAACTACGGGGTTGGTGAGAGCTTCACAGTGCAGCGG

CGAGTTGAGCCTAAGGTGACTGTGTATCCTTCAAAGACCCAGCCCCTGCAGCACCACAACCTCCTGGTCTGC

TCTGTGAGTGGTTTCTATCCAGGCAGCATTGAAGTCAGGTGGTTCCGGAACGGCCAGGAAGAGAAGGCTGGG

GTGGTGTCCACAGGCCTGATCCAGAATGGAGATTGGACCTTCCAGACCCTGGTGATGCTGGAAACAGTTCCT

CGGAGTGGAGAGGTTTACACCTGCCAAGTGGAGCACCCAAGTGTGACGAGCCCTCTCACAGTGGAATGGAGA

GCACGGTCTGAATCTGCACAGAGCAAGATGCTGAGTGGAGTCGGGGGCTTCGTGCTGGGCCTGCTCTTCCTT

GGGGCCGGGCTGTTCATCTACTTCAGGAATCAGAAAGGACACTCTGGACTTCAGCCAACAGGATTCCTGAGC

TGA

<gms:automated_annotation>
            <gms:length sequence="1">0</gms:length>

<gms:bases_so_far sequence="1">0</gms:bases_so_far>

<gms:invalid_dna_symbols>
            </gms:invalid_dna_symbols>

<gms:agct_count>a171 g263 c200
t167</gms:agct_count>

<gms:agct_ratio>a21% g33% c25%
t21%</gms:agct_ratio>

<gms:gene sequence="HLA664,DRB1*11,81 bases,
8C9FCB6 checksum" />

<gms:t_cell_epitopes>
              <gms:protein>pkyvkqntlkla {treat as
peptide}</gms:protein>

<gms:protein>gplkaeiaqrle {treat as
peptide}</gms:protein>
            </gms:t_cell_epitopes>

<gms:orf>ATGGTGTGTCTGAAGCTCCCTGGAGGCTCCTGCATGACAGCGCTGACAGTGACACTGATGGTG

CTGAGCTCCCCACTGGCTTTGGCTGGG
```

-continued

<gms:experimental_start_of_mature_peptide />

GACACCCGACCACGTTTCTTGTGGCAGCTTAAGTTTGAATGTCATTTCTTCAATGGGACGGAGCGGGTGCGG

TTGCTGGAAAGATGCATCTATAACCAAGAGGAGTCCGTGCGCTTCGACAGCGACGTG

<gms:snp>GGG</gms:snp>

GAGTACC

<gms:transcription_factor>GGGCGG</gms:transcription_factor>

TGACGGAGCTG

<gms:transcription_factor>GGGCGG</gms:transcription_factor>

CCTGATGCCGAGTACTGGAACAGCCAGAAGGACCTCCTGGAGCAGAGGCGGGCCGCGGTGGACACCTACTGC

AGACACAACTACGGGGTTGGTGAGAGCTTCACAGTGCAGCGGCGAGTTGAGCCTAAGGTGACTGTGTATCCT

TCAAAGACCCAGCCCCTGCAGCACCACAACCTCCTGGTCTGCTCTGTGAGTGGTTTCTATCCAGGCAGCATT

GAAGTCAGGTGGTTCCGGAACGGCCAGGAAGAGAAGGCTGGGGTGGTGTCCACAGGCCTGATCCAGAATGGA

GATTGGACCTTCCAGACCCTGGTGATGCTGGAAACAGTTCCTCGGAGTGGAGAGGTTTACACCTGCCAAGTG

GAGCACCCAAGTGTGACGAGCCCTCTCACAGTGGAATGGAGAGCACGGTCTGAATCTGCACAGAGCAAGATG

CTGAGTGGAGTCGGGGGCTTCGTGCTGGGCCTGCTCTTCCTTGGGGCCGGGCTGTTCATCTACTTCAGGAAT

CAGAAAGGACACTCTGGACTTCAGCCAACAGGATTCCTGAGCTGA</gms:orf>

<gms:dna_feature type="whole_sequence" sequence="1" start="1" stop="801" />

<gms:dna_feature type="gene sequence=HLA664,DRB1*11, 81 bases, 8C9FCB6 checksum/" sequence="1" start="1" />

<gms:dna_feature type="t_cell_epitopes" sequence="1" start="0" stop="0" />

<gms:dna_feature type="protein" sequence="1" start="0" stop="0" />

<gms:dna_feature type="protein" sequence="1" start="0" stop="0" />

<gms:dna_feature type="orf" sequence="1" start="1" stop="801" />

<gms:dna_feature type="experimental_start_of_mature_peptide/" sequence="1" start="91" />

<gms:dna_feature type="snp" sequence="1" start="220" stop="222" />

<gms:dna_feature type="transcription_factor" sequence="1" start="230" stop="235" />

<gms:dna_feature type="transcription factor" sequence="1" start="247" stop="252" />

<gms:protein_sequence sequence="1" readingframe="1" length="267" >MVCLKLPGGSCMTALTVTLMVLSSPLALAGDTRPRFLWQLKFECHFFNGT

RVRLLERCIYNQEESVRFDSDVGEYRAVTELGRPDAEYWNSQKDLLEQRR

AVDTYCRHNYGVGESFTVQRRVEPKVTVYPSKTQPLQHHNLLVCSVSGFY

GSIEVRWFRNGQEEKAGVVSTGLIQNGDWTFQTLVMLETVPRSGEVYTCQ

EHPSVTSPLTVEWRARSESAQSKMLSGVGGFVLGLLFLGAGLFIYFRNQK

HSGLQPTGFLS.</gms:protein_sequence>

<gms:protein_annotation>
  <gms:translation sequence="1" readingframe="1">
  <gms:gene sequence="HLA00664,DRB1*0101,801

-continued bases, 80C9FCB6 checksum" />

<gms:t_cell_epitopes>
        <gms:protein>pkyvkqntlkla {treat as peptide} </gms:protein>

<gms:protein>gplkaeiaqrle {treat as peptide}</gms:protein>
      </gms:t_cell_epitopes>

MVCLKLPG

<gms:myristyl>GSCMTA</gms:myristyl>

LTVTLMVLSSPLALA

<gms:experimental_start_of_mature_peptide />

GDTRPRFLWQLKFECHFF

<gms:glycosylation>NGT</gms:glycosylation>

RV

<gms:tyrosine_phosphorylation>RLLERCIY</gms:tyrosine_phosphorylation>

NQEE

<gms:pkc_phosphorylation>SVR</gms:pkc_phosphorylation>

FDSD

<gms:snp>V</gms:snp>

GEYRAVTELGRPDAEYWN

<gms:pkc_phosphorylation>SQK</gms:pkc_phosphorylation>

DLLEQRRAAVDTYCRHNY

<gms:myristyl>GVGESF</gms:myristyl>

TVQRRVEPKVTVYPSKTQPLQHHNLLVCSVSGFYPGSIEVRWFRNGQEEKA

<gms:myristyl>GVVSTG</gms:myristyl>

LIQNGDWTFQTLVMLETVPRSGEV

<gms:ig_histocompat_sig>YTCQVEH</gms:ig_histocompat_sig>

PSVTSPLTVEWRARSESAQSKML

<gms:glycosaminoglycan>SGVG</gms:glycosaminoglycan>

GFVLGLLFLGAGLFIYFRNQKGHS

<gms:myristyl>GLQPTG</gms:myristyl>

FLS.

<gms:protein_feature type="whole_sequence" sequence="1" context="protein-sized entity" readingframe="1" start="1" stop="265" />

<gms:protein_feature type="gene sequence=HLA00664,DRB1*0101,801 bases, 80C9FCB6 checksum/" sequence="1" readingframe="1" start="1" />

<gms:protein_feature type="t_cell_epitopes" sequence="1" readingframe="1" start="0" stop="0" />

<gms:protein_feature type="protein" sequence="1" readingframe="1" start="0" stop="0" />

<gms:protein_feature type="protein" sequence="1" readingframe="1" start="0" stop="0" />

<gms:protein_feature type="myristyl" sequence="1" readingframe="1" start="9" stop="14" />

-continued

```
            <gms:protein_feature
type="experimental_start_of_mature_peptide/" sequence="1"
readingframe="1" start="30" /> gms:protein_feature type="glycosylation"
sequence="1" readingframe="1" start="48" stop="50" />

<gms:protein_feature
type="tyrosine_phosphorylation" sequence="1" readingframe="1" start="53"
stop="60" />

<gms:protein_feature type="pkc_phosphorylation"
sequence="1" readingframe="1" start="65" stop="67" />

<gms:protein_feature type="snp" sequence="1"
readingframe="1" start="72" stop="72" />

<gms:protein_feature type="pkc_phosphorylation"
sequence="1" readingframe="1" start="91" stop="93" />

<gms:protein_feature type="myristyl"
sequence="1" readingframe="1" start="112" stop="117" />

<gms:protein_feature type="myristyl"
sequence="1" readingframe="1" start="169" stop="174" />

<gms:protein_feature type="ig_histocompat_sig"
sequence="1" readingframe="1" start="199" stop="205" />

<gms:protein_feature type="glycosaminoglycan"
sequence="1" readingframe="1" start="229" stop="232" />

<gms:protein_feature type="myristyl"
sequence="1" readingframe="1" start="257" stop="262" />

</gms:translation>
            <gms:protein_sequence sequence="1"
readingframe="1 complement"
length="135">SAQESCWLKSRVSFLIPEVDEQPGPKEEQAQHEAPDSTQHLALCRFRPCS

FHCERARHTWVLHLAGVNLSTPRNCFQHHQGLEGPISILDQACGHHPSLL

LAVPEPPDFNAAWIETTHRADQEVVVLQGLGL.</gms:protein_sequence>

<gms:translation sequence="1" readingframe="1
complement">

<gms:gene sequence="HLA00664,DRB1*0101, 801
bases, 80C9FCB6 checksum" />

<gms:t_cell_epitopes>
               <gms:protein>pkyvkqntlkla {treat as
peptide}</gms:protein>

<gms:protein>gplkaeiaqrle {treat as
peptide}</gms:protein>
            </gms:t_cell_epitopes>

<gms:st_phosphorylation>SAQE</gms:st_phosphorylation>

SCWLKSRVSFLIPEVDEQPGPKEEQ

<gms:experimental_start_of_mature_peptide />

AQHEAPDSTQHLALCRFRPCSPFHCERARHTWVLHLAGV

<gms:glycosylation>NLS</gms:glycosylation>

<gms:snp>P</gms:snp>

RNCFQHHQGLEGPI

<gms:st_phosphorylation>SILD</gms:st_phosphorylation>

QACGHHPSLLFLAVPEPPDFNAAWIET

<gms:pkc_phosphorylation>THR</gms:pkc_phosphorylation>

ADQEVVVLQGLGL.
```

-continued
```
            <gms:protein_feature type="whole_sequence"
sequence="1" context="protein-sized entity" readingframe="1 complement"
start="1" stop="133" />

<gms:protein_feature type="gene
sequence=HLA00664,DRB1*0101,801 bases, 80C9FCB6 checksum/" sequence="1"
readingframe="1 complement" start="1"/>

<gms:protein_feature type="t_cell_epitopes"
sequence="1" readingframe="1 complement" start="0" stop="0" />

<gms:protein_feature type="protein" sequence="1"
readingframe="1 complement" start="0" stop="0" />

<gms:protein_feature type="protein" sequence="1"
readingframe="1 complement" start="0" stop="0" />

<gms:protein_feature type="st_phosphorylation"
sequence="1" readingframe="1 complement" start="1" stop="4" />

<gms:protein_feature
type="experimental_start_of_mature_peptide/" sequence="1"
readingframe="1 complement" start="30" />

<gms:protein_feature type="glycosylation"
sequence="1" readingframe="1 complement" start="69" stop="71" />

<gms:protein_feature type="snp" sequence="1"
readingframe="1 complement" start="72" stop="72" />

<gms:protein_feature type="st_phosphorylation"
sequence="1" readingframe="1 complement" start="87" stop="90" />

<gms:protein_feature type="pkc_phosphorylation"
sequence="1" readingframe="1 complement" start="118" stop="120" />

</gms:translation>
            <gms:protein_sequence sequence="1"
readingframe="2" length="4">WCV.</gms:protein_sequence>

<gms:translation sequence="1" readingframe="2">
            <gms:gene sequence="HLA00664,DRB1*0101, 801
bases, 80C9FCB6 checksum" />

<gms:t_cell_epitopes>
                <gms:protein>pkyvkqntlkla {treat as
peptide}</gms:protein>

<gms:protein>gplkaeiaqrle {treat as
peptide}</gms:protein>

</gms:t_cell_epitopes>

WCV

<gms:stop_codon></gms:stop_codon>
<gms:protein_feature type="whole_sequence"
sequence="1" context="binding peptide? " readingframe="2" start="1"
stop="3" />

<gms:protein_feature type="gene
sequence=HLA00664,DRB1*0101, 801 bases, 80C9FCB6 checksum/" sequence="1"
readingframe="2" start="1" />

<gms:protein_feature type="t_cell_epitopes"
sequence="1" readingframe="2" start="0" stop="0" />

<gms:protein_feature type="protein" sequence="1"
readingframe="2" start="0" stop="0" />

<gms:protein_feature type="protein" sequence="1"
readingframe="2" start="0" stop="0" />

<gms:protein_feature type="stop_codon"
sequence"1" readingframe="2" start="4" stop="3" />
```

-continued
```
            </gms:translation>
            <gms:protein_sequence sequence="1"
readingframe="2 complement"
length="135" >SAQESCWLKSRVSFLIPEVDEQPGPKEEQAQHEAPDSTQHLALCRFRPCS

FHCERARHTWVLHLAGVNLSTPRNCFQHHQGLEGPISILDQACGHHPSLL

LAVPEPPDFNAAWIETTHRADQEVVVLQGLGL.</gms:protein_sequence>

<gms:translation sequence="1" readingframe="2
complement">
            <gms:gene sequence="HLA00664,DRB1*0101, 801
bases, 80C9FCB6 checksum" />

<gms:t_cell_epitopes>
              <gms:protein>pkyvkqntlkla {treat as
peptide}</gms:protein>

<gms:protein>gplkaeiaqrle {treat as
peptide}</gms:protein>
            </gms:t_cell_epitopes>

<gms:st_phosphorylation>SAQE</gms:st_phosphorylation>

SCWLKSRVSFLIPEVDEQPGPKEEQ

<gms:experimental_start_of_mature_peptide />

AQHEAPDSTQHLALCRFRPCSPFHCERARHTWVLHLAGV

<gms:glycosylation>NLS</gms:glycosylation>

<gms:snp>P</gms:snp>

RNCFQHHQGLEGPI

<gms:st_phosphorylation>SILD</gms:st_phosphorylation>

QACGHHPSLLFLAVPEPPDFNAAWIET

<gms:pkc_phosphorylation>THR</gms:pkc_phosphorylation>

ADQEVVVLQGLGL.

<gms:protein_feature type="whole_sequence"
sequence="1" context="protein-sized entity" readingframe="2 complement"
start="1" stop="133" />

<gms:protein_feature type="gene
sequence=HLA00664,DRB1*0101, 801 bases, 80C9FCB6 checksum/" sequence="1"
readingframe="2 complement" start="1" />

<gms:protein_feature type="t_cell_epitopes"
sequence="1" readingframe="2 complement" start="0" stop="0" />

<gms:protein_feature type="protein" sequence="1"
readingframe="2 complement" start="0" stop="0" />

<gms:protein_feature type="protein" sequence="1"
readingframe="2 complement" start="0" stop="0" />

<gms:protein_feature type="st_phosphorylation"
sequence="1" readingframe="2 complement" start="1" stop="4" />

<gms:protein_feature
type="experimental_start_of_mature_peptide/" sequence="1"
readingframe="2 complement" start="30" />

<gms:protein_feature type="glycosylation"
sequence="1" readingframe="2 complement" start="69" stop="71" />

<gms:protein_feature type="snp" sequence="1"
readingframe="2 complement" start="72" stop="72" />

<gms:protein_feature type="st_phosphorylation"
sequence="1" readingframe="2 complement" start="87" stop="90" />

<gms:protein_feature type="pkc_phosphorylation"
sequence="1" readingframe="2 complement" start="118" stop="120" />
```

-continued

```
            </gms:translation>
            <gms:protein_sequence sequence="1"
readingframe="3"
length="40" >GVSEAPWRLLHDSADSDTDGAELPTGFGWGHPTTFLVAA.</gms:protein_sequen
ce>

<gms:translation sequence="1" readingframe="3">
            <gms:gene sequence="HLA00664,DRB1*0101, 801
bases, 80C9FCB6 checksum" />

<gms:t_cell_epitopes>
                <gms:protein>pkyvkqntlkla {treat as
peptide}</gms:protein>

<gms:protein>gplkaeiaqrle {treat as
peptide}</gms:protein>

</gms:t_cell_epitopes>

GVSEAPWRLLHDSAD

<gms:st_phosphorylation>SDTD</gms:st_phosphorylation>

GAELPTGFGW

<gms:experimental_start_of_mature_peptide />

GHPTTFLVAA

<gms:stop_codon>.</gms:stop_codon>

<gms:protein_feature type="whole_sequence"
sequence="1" context="protein-sized entity" readingframe="3" start="1"
stop="39" />

<gms:protein_feature type="gene
sequence=HLA00664,DRB1*0101, 801 bases, 80C9FCB6 checksum/" sequence="1"
readingframe="3" start="1" />

<gms:protein_feature type="t_cell_epitopes"
sequence="1" readingframe="3" start="0" stop="0" />

<gms:protein_feature type="protein" sequence="1"
readingframe="3" start="0" stop="0" />

<gms:protein_feature type="protein" sequence="1"
readingframe="3" start="0" stop="0" />

<gms:protein_feature type="st_phosphorylation"
sequence="1" readingframe="3" start="16" stop="19" />

<gms:protein_feature
type="experimental_start_of_mature_peptide/" sequence="1"
readingframe="3" start="30" />

<gms:protein_feature type="stop_codon"
sequence="1" readingframe="3" start="40" stop="39" />

</gms:translation>

<gms:protein_sequence sequence="1"
readingframe="3 complement"
length="135">SAQESCWLKSRVSFLIPEVDEQPGPKEEQAQHEAPDSTQHLALCRFRPCS

FHCERARHTWVLHLAGVNLSTPRNCFQHHQGLEGPISILDQACGHHPSLL

LAVPEPPDFNAAWIETTHRADQEVVVLQGLGL.</gms:protein_sequence>

<gms:translation sequence="1" readingframe="3
complement">

<gms:gene sequence="HLA00664,DRB1*0101, 801
bases, 80C9FCB6 checksum" />

<gms:t_cell_epitopes>
                <gms:protein>pkyvkqntlkla {treat as
peptide}</gms:protein>

<gms:protein>gplkaeiaqrle {treat as
peptide}</gms:protein>
```

-continued

```
        </gms:t_cell_epitopes>

<gms:st_phosphorylation>SAQE</gms:st_phosphorylation>

SCWLKSRVSFLIPEVDEQPGPKEEQ

<gms:experimental_start_of_mature_peptide />

AQHEAPDSTQHLALCRFRPCSPFHCERARHTWVLHLAGV

<gms:glycosylation>NLS</gms:glycosylation>

<gms:snp>P</gms:snp>

RNCFQHHQGLEGPI

<gms:st_phosphorylation>SILD</gms:st_phosphorylation>

QACGHHPSLLFLAVPEPPDFNAAWIET

<gms:pkc_phosphorylation>THR</gms:pkc_phosphorylation>

ADQEVVVLQGLGL.

<gms:protein_feature type="whole_sequence"
sequence="1" context="protein-sized entity" readingframe="3 complement"
start="1" stop="133" />

<gms:protein_feature type="gene
sequence=HLA00664,DRB1*0101, 801 bases, 80C9FCB6 checksum/" sequence="1"
readingframe="3 complement" start="1" />

<gms:protein_feature type="t_cell_epitopes"
sequence="1" readingframe="3 complement" start="0" stop="0" />

<gms:protein_feature type="protein" sequence="1"
readingframe="3 complement" start="0" stop="0" />

<gms:protein_feature type="protein" sequence="1"
readingframe="3 complement" start="0" stop="0" />

<gms:protein_feature type="st_phosphorylation"
sequence="1" readingframe="3 complement" start="1" stop="4" />

<gms:protein_feature
type="experimental_start_of_mature_peptide/" sequence="1"
readingframe="3 complement" start="30" />

<gms:protein_feature type="glycosylation"
sequence="1" readingframe="3 complement" start="69" stop="71" />

<gms:protein_feature type="snp" sequence="1"
readingframe="3 complement" start="72" stop="72" />

<gms:protein_feature type="st_phosphorylation"
sequence="1" readingframe="3 complement" start="87" stop="90" />

<gms:protein_feature type="pkc_phosphorylation"
sequence="1" readingframe="3 complement" start="118" stop="120" />

</gms:translation>
      </gms:protein_annotation>
    </gms:automated_annotation>
  </gms:dna>

<gms:dna sequence="2" base="802" locus="1">
  <gms:annotation>possible somatic mutation cell line #4
end-11th</gms:annotation>

AGGAATCAGAAAGGACACTCTGGACTTCAGCCAACAGGATACCTGAGCTGA

<gms:automated_annotation>
    <gms:length sequence="2">51</gms:length>

<gms:bases_so_far sequence="2">51</gms:bases_so_far>

<gms:invalid_dna_symbols>
    </gms:invalid_dna_symbols>
```

-continued
```
    <gms:agct_count>a18 g13 c12 t8</gms:agct_count>

<gms:agct_ratio>a35% g25% c24% 16%</gms:agct_ratio>

AGGAATCAGAAAGGACACTCTGGACTTCAGCCAACAGGATACCTGAGCTGA

<gms:dna_feature type="whole_sequence" sequence="2"
start="1" stop="51" />

<gms:protein_sequence sequence="2" readingframe="1"
length="17" >RNQKGHSGLQPTGYLS.</gms:protein_sequence>

<gms:protein_annotation>
        <gms:translation sequence="2"
readingframe="1">RNQKGHS
        <gms:myristyl>GLQPTG</gms:myristyl>

YLS.

<gms:protein_feature type="whole_sequence"
sequence="2" context="binding peptide? " readingframe="1" start="1"
stop="16" />

<gms:protein_feature type="myristyl" sequence="2"
readingframe="1" start="8" stop="13" />
        </gms:translation>

<gms:protein_sequence sequence="2" readingframe="1
complement" length="17">SAQVSCWLKSRVSFLIP</gms:protein_sequence>

<gms:translation sequence="2" readingframe="1
complement" >SAQVSCWLKSRVSFLIP

<gms:protein_feature type="whole_sequence"
sequence="2" context="binding peptide? " readingframe="1 complement"
start="1" stop="17" />
        </gms:translation>

<gms:protein_sequence sequence="2" readingframe="2"
length="15" >GIRKDTLDFSQQDT.</gms:protein_sequence>

<gms:translation sequence="2"
readingframe="2" >GIRKDTLDF

<gms:st_phosphorylation>SQQD</gms:st_phosphorylation>

T.

<gms:protein_feature type="whole_sequence"
sequence="2" context="binding peptide? " readingframe="2" start="1"
stop="14" />

<gms:protein_feature type="st_phosphorylation"
sequence="2" readingframe="2" start="10" stop="13" />
        </gms:translation>

<gms:protein_sequence sequence="2" readingframe="2
complement" length="18">SAQVSCWLKSRVSFLIcc</gms:protein_sequence>

<gms:translation sequence="2" readingframe="2
complement" >SAQVSCWLKSRVSFLIcc

<gms:protein_feature type="whole_sequence"
sequence="2" context="binding peptide?" readingframe="2 complement"
start="1" stop="16" />
        </gms:translation>

<gms:protein_sequence sequence="2" readingframe="3"
length="17" >ESERTLWTSANRIPELa</gms:protein_sequence>

<gms:translation sequence="2" readingframe="3">E
<gms:pkc_phosphorylation>SER</gms:pkc_phosphorylation>

TLWTSANRIPELa

<gms:protein_feature type="whole_sequence"
sequence="2" context="binding peptide? " readingframe="3" start="1"
stop="16" />
```

```
                                           -continued
           <gms:protein_feature type="pkc_phosphorylation"
sequence="2" readingframe="3" start="2" stop="4" />
              </gms:translation>

<gms:protein_sequence sequence="2" readingframe="3
complement" length="17" >SAQVSCWLKSRVSFLIc</gms:protein_sequence>

<gms:translation sequence="2" readingframe="3
complement" >SAQVSCWLKSRVSFLIc

<gms:protein_feature type="whole_sequence"
sequence="2" context="binding peptide? " readingframe="3 complement"
start="1" stop="16" />
              </gms:translation>
           </gms:protein_annotation>
         </gms:automated_annotation>
         </gms:dna>

<gms:dna sequence="3" base="853"
locus="1">{end}</gms:dna>

<gms:dna_checks>accumulative basepair count=852,
sequences=2</gms:dna_checks>
         </gms:genomic_data>
       </cda:local_markup>
     </cda:content>
   </cda:paragraph>
 </cda:section>
</leveltwo>
```

What is claimed is:

1. A computer-based method for processing data that includes a genomic sequence, said method comprising:
   identifying at least one genomic base in an input data stream comprising said genomic sequence;
   assigning a base-specific binary code to the at least one genomic base;
   grouping the base-specific binary code to form a genomic data stream representative of the genomic sequence;
   assigning a command binary code to at least one command for selectively processing said genomic data stream; and
   integrating said genomic data stream and said command binary code to form an output binary data stream.

2. The method of claim 1, wherein said input data stream further comprises clinical data.

3. The method of claim 2, wherein said output binary data stream comprises said clinical data.

4. The method of claim 1, wherein said input data stream is read from an input data file.

5. The method of claim 1, further comprising transmitting said output binary stream to a receiving data processing system.

6. The method of claim 5, further comprising writing said output binary data stream to a binary data file before said transmitting step.

7. The method of claim 5, wherein said receiving data processing system performs the steps of:
   parsing the genomic data stream from the output binary data stream;
   unpacking the base-specific binary code within the genomic data stream;
   reassigning said genomic bases to said base-specific binary code; and
   arranging the genomic bases to form an output data sequence that includes said genomic sequence.

8. The method of claim 7, further comprising writing said output data sequence to an output data file.

9. The method of claim 1, wherein said genomic sequence is a DNA sequence and wherein said genomic base is one of adenine, guanine, cytosine, and thymine.

10. The method of claim 1, wherein said genomic sequence is an RNA sequence, and wherein said genomic base is one of adenine, guanine, cytosine, and uracil.

11. The method of claim 1, wherein the base-specific binary code is an n-bit binary code, wherein $2 \leq n \leq 6$.

12. The method of claim 1, wherein the base-specific binary code is a 2-bit binary code.

13. The method of claim 12, wherein the 2-bit base-specific binary code is one of 00, 01, 10, or 11.

14. The method of claim 1, wherein the base-specific binary code comprises a code group of genomic bases, wherein $2^n$ is greater than or equal to the number of permutations possible for the code group of genomic bases, and wherein n equals a number of bits necessary to code said code group of genomic bases.

15. The method of claim 14, wherein the code group comprises two genomic bases thereby forming 16 possible permutations of the two genomic bases, and wherein the number of bits necessary to code the code group comprising the two genomic bases is 4.

16. The method of claim 1, wherein said grouping step comprises grouping said base-specific binary code into at least one byte.

17. The method of claim 16, wherein said byte is an 8-bit byte.

18. The method of claim 17, wherein said byte comprises a genomic base portion coding for at least one genomic base and a command portion coding for at least one command.

19. The method of claim 18, wherein said command portion is a 6-bit command portion.

20. The method of claim 18, wherein said genomic base portion comprises a 6-bit base portion and wherein said command portion comprises a 2-bit command portion.

21. The method of claim 1, wherein the binary code is a 2-bit binary code, and wherein the 2-bit binary code is packed into a binary stream of at least one 8-bit byte.

22. The method of claim 21, wherein X number of bases represented by said 2-bit binary code are grouped into said 8-bit byte wherein X=1, 2, or 3; and wherein any remaining bits of said 8-bit byte are used to specify a multiplicity of the X number of bases represented by said 2-bit binary code.

23. The method of claim 21, wherein four genomic bases represented by said 2-bit binary code are grouped into said 8-bit byte, and wherein a multiplicity of the four bases is specified elsewhere in said output binary data stream.

24. The method of claim 1, wherein said assigning a base-specific binary code comprises assigning a first bit to said genomic base such that the first bit corresponds to a purine or a pyrimidine base.

25. The method of claim 4, further comprising encrypting said output binary data stream.

26. The method of claim 25, further comprising decrypting said binary stream after said transmitting step.

27. The method of claim 1, wherein said command comprises annotation text annotating said one or more genomic bases.

28. The method of claim 27, wherein said annotation text is embedded in said output binary data stream so as to preserve a relationship of said annotation text to said genomic bases.

29. The method of claim 28, further comprising transmitting said output binary data stream to a receiving data processing system and extracting said annotation text from said output binary data stream after said transmitting step so as to preserve the relationship of said annotation text to said genomic bases.

30. The method of claim 5, wherein said command is operable to add a text identifier to said genomic data stream.

31. The method of claim 30, further comprising providing a corresponding text identifier to a user of said receiving data processing system.

32. The method of claim 1, wherein said command is operable to provide validation of integrity of said genomic data stream.

33. The method of claim 1, wherein said command is operable to exclude identifying information pertaining to a person whose genomic sequence is contained in said genomic data stream from being revealed in said output binary data stream.

34. The method of claim 1, wherein said command is operable to control a level of encryption of the output binary data stream.

35. The method of claim 34, wherein said command is recognized by a receiving data processing system to permit decryption of the output binary data stream.

36. The method of claim 34, wherein said command is operable to seed an algorithm used for encryption of the output binary data stream.

37. The method of claim 34, wherein said command is operable to specify a block size of a shuffling algorithm used for encryption of the output binary data stream.

38. The method of claim 1, wherein said command is operable to embed program code for selectively processing said genomic data stream.

39. The method of claim 1, wherein said command is operable to bracket at least one portion of said genomic data stream thereby selecting said portion for processing.

40. An apparatus in a data processing system for transferring data comprising a genomic sequence, said apparatus comprising:

at least one processor operative to: (i) identify at least one genomic base in an input data stream comprising said genomic sequence; (ii) assign a base-specific binary code to the at least one genomic base; (iii) group the base-specific binary code to form a genomic data stream representative of the genomic sequence; (iv) assign a command binary code to at least one command for selectively processing said genomic data stream; and (v) integrate said genomic data stream and said command binary code to form an output binary data stream.

41. An article of manufacture in a data processing system for transferring data comprising a genomic sequence, said article of manufacture comprising a machine readable medium containing one or more programs which when executed implement the steps of:

identifying at least one genomic base in an input data stream comprising said genomic sequence;

assigning a base-specific binary code to the at least one genomic base;

grouping the base-specific binary code to form a genomic data stream representative of the genomic sequence;

assigning a command binary code to at least one command for selectively processing said genomic data stream; and integrating said genomic data stream and said command binary code to form an output binary data stream.

* * * * *